US012672771B2

(12) United States Patent     (10) Patent No.:   US 12,672,771 B2

Jen et al.     (45) Date of Patent:     Jul. 7, 2026

(54) DELIVERY SYSTEMS AND DEVICES FOR THE TREATMENT OF BENIGN PROSTATIC HYPERPLASIA AND RELATED LOWER URINARY TRACT SYMPTOMS

(71) Applicant: Prodeon Medical Corporation, Taipei (TW)

(72) Inventors: Jimmy Jen, Saratoga, CA (US); Gary Daniel Zaretzka, Sunnyvale, CA (US); Kenneth Chih-Ping Chang, San Jose, CA (US); Kondapavulur T. Venkateswara-Rao, San Jose, CA (US)

(73) Assignee: Prodeon Medical Corporation, Taipei (TW)

( * ) Notice: Subject to any disclaimer, the term of this patent is extended or adjusted under 35 U.S.C. 154(b) by 1115 days.

(21) Appl. No.: 17/066,740

(22) Filed: Oct. 9, 2020

(65) Prior Publication Data

US 2021/0022594 A1     Jan. 28, 2021

Related U.S. Application Data

(63) Continuation-in-part of application No. 15/972,031, filed on May 4, 2018, now Pat. No. 11,497,637.

(Continued)

(51) Int. Cl.
   *A61B 1/307*      (2006.01)
   *A61B 1/00*      (2006.01)
   (Continued)

(52) U.S. Cl.
   CPC .......... *A61B 1/307* (2013.01); *A61B 1/00133* (2013.01); *A61B 1/00135* (2013.01);
   (Continued)

(58) Field of Classification Search
   CPC . A61B 1/307; A61B 1/00133; A61B 1/00135; A61B 2017/00274;
   (Continued)

(56) References Cited

U.S. PATENT DOCUMENTS 4,973,301 A    11/1990   Nissenkorn
5,290,294 A   *   3/1994   Cox ....................... A61B 17/29
                                   606/205

(Continued)

FOREIGN PATENT DOCUMENTS

CN     106466194 A    3/2017
CN     107847324 A    3/2018

(Continued)

OTHER PUBLICATIONS

Storz, Carl, "Extract From the Pediatric Surgery Catalog Urology," Jan. 2019, retrieved on Dec. 11, 2020, from https://karlstorz.com/cps/rde/xbcr/karlstorz_assets/ASSETS/3597875.

(Continued)

*Primary Examiner* — Tan-Uyen T Ho
*Assistant Examiner* — Osama Nemer
(74) *Attorney, Agent, or Firm* — Dergosits & Noah LLP; Todd A. Noah

(57) ABSTRACT

Devices and systems are disclosed for managing and/or treating body tissues obstructing a hollow body lumen, including the prostatic lobe tissues obstructing the urethra, for example conditions including benign prostatic hyperplasia (BPH), bladder outlet obstruction (BOO), benign prostatic obstruction (BPO) and associated lower urinary tract symptoms (LUTS). An implant is maintained in a constrained configuration within a distal portion of an elongated sheath so that is may be deployed by driving the implant (Continued)

with a pusher coaxially disposed within the sheath. An implant engaging element helps maintain control of the implant during deployment.

28 Claims, 11 Drawing Sheets

Related U.S. Application Data

(60) Provisional application No. 62/912,759, filed on Oct. 9, 2019.

(51) Int. Cl.
A61B 17/00 (2006.01)
A61F 2/95 (2013.01)
A61F 2/966 (2013.01)

(52) U.S. Cl.
CPC ............ *A61F 2/9517* (2020.05); *A61F 2/966* (2013.01); *A61B 2017/00274* (2013.01)

(58) Field of Classification Search
CPC .... A61B 2017/32096; A61B 17/12118; A61B 5/6862; A61F 2/9517; A61F 2/966; A61F 2230/001; A61F 2/962; A61F 2/86; A61F 2002/047; A61F 2002/9528; A61F 2230/0073; A61F 2/95
See application file for complete search history.

(56) References Cited

U.S. PATENT DOCUMENTS

| | | | | |
|---|---|---|---|---|
| 5,518,498 | A | 5/1996 | Lindenberg et al. | |
| 5,601,591 | A * | 2/1997 | Edwards .................. | A61F 2/88 |
| | | | | 606/198 |
| 5,830,179 | A | 11/1998 | Mikus et al. | |
| 6,391,033 | B2 * | 5/2002 | Ryan ......................... | A61F 2/91 |
| | | | | 623/1.46 |
| 7,169,172 | B2 * | 1/2007 | Levine ...................... | A61F 2/95 |
| | | | | 623/1.11 |
| 8,343,205 | B2 | 1/2013 | Sugimoto et al. | |
| 8,652,193 | B2 * | 2/2014 | Dorn ........................ | A61F 2/966 |
| | | | | 606/151 |
| 8,801,746 | B1 * | 8/2014 | Kreidler ............. | A61B 17/1215 |
| | | | | 606/200 |
| 9,848,905 | B2 | 12/2017 | Kilemnik | |
| 9,956,103 | B2 | 5/2018 | Slazas et al. | |
| 10,321,923 | B2 * | 6/2019 | DeGraaf ................. | A61B 1/018 |
| 10,517,722 | B2 * | 12/2019 | Passman ............... | A61F 2/2436 |
| 10,758,717 | B2 | 9/2020 | Gianotti et al. | |
| 10,952,851 | B2 | 3/2021 | Marchand | |
| 10,980,858 | B2 | 4/2021 | Nakamura et al. | |
| 11,096,774 | B2 * | 8/2021 | Sicotte ................... | A61F 2/885 |
| 11,464,542 | B2 * | 10/2022 | Rosenthal ............... | A61F 2/186 |
| 11,707,371 | B2 * | 7/2023 | Becking .................. | A61F 2/95 |
| | | | | 623/1.11 |
| 2002/0007206 | A1 | 1/2002 | Bui et al. | |
| 2004/0087965 | A1 * | 5/2004 | Levine ...................... | A61F 2/95 |
| | | | | 623/1.11 |
| 2004/0230131 | A1 * | 11/2004 | Kassab .................. | A61B 5/036 |
| | | | | 600/587 |
| 2005/0015111 | A1 | 1/2005 | McGuckin et al. | |
| 2005/0027305 | A1 | 2/2005 | Shiu et al. | |
| 2005/0038470 | A1 | 2/2005 | van der Burg et al. | |
| 2005/0119721 | A1 | 6/2005 | Rabkin et al. | |
| 2005/0154439 | A1 * | 7/2005 | Gunderson ............. | A61F 2/966 |
| | | | | 623/1.11 |
| 2006/0136035 | A1 * | 6/2006 | Hermann .................. | A61F 2/88 |
| | | | | 623/1.11 |
| 2006/0282150 | A1 * | 12/2006 | Olson .............. | A61M 25/0136 |
| | | | | 623/1.11 |
| 2007/0156225 | A1 * | 7/2007 | George ..................... | A61F 2/95 |
| | | | | 606/108 |

| | | | | |
|---|---|---|---|---|
| 2007/0219466 | A1 * | 9/2007 | Tremulis .......... | A61M 25/0082 |
| | | | | 600/585 |
| 2008/0172084 | A1 * | 7/2008 | Kusleika ................... | A61F 2/01 |
| | | | | 606/151 |
| 2009/0099650 | A1 * | 4/2009 | Bolduc ................. | A61B 17/064 |
| | | | | 623/1.36 |
| 2009/0132033 | A1 * | 5/2009 | Maurer .................. | A61F 2/2442 |
| | | | | 623/2.11 |
| 2009/0156977 | A1 | 6/2009 | Daignault et al. | |
| 2009/0204005 | A1 | 8/2009 | Keast et al. | |
| 2009/0306703 | A1 | 12/2009 | Germanovich et al. | |
| 2010/0049313 | A1 * | 2/2010 | Alon ...................... | A61F 2/2436 |
| | | | | 623/2.11 |
| 2010/0087705 | A1 * | 4/2010 | Byers .................... | A61M 39/06 |
| | | | | 600/104 |
| 2010/0130815 | A1 * | 5/2010 | Gross ........................ | A61F 2/92 |
| | | | | 600/30 |
| 2010/0256735 | A1 * | 10/2010 | Morales, Jr. .............. | A61F 2/90 |
| | | | | 623/1.22 |
| 2010/0274346 | A1 | 10/2010 | Chouinard et al. | |
| 2011/0077676 | A1 | 3/2011 | Sivan et al. | |
| 2011/0276081 | A1 | 11/2011 | Kilemnik | |
| 2012/0029281 | A1 * | 2/2012 | Frassica ............ | A61M 25/0068 |
| | | | | 600/114 |
| 2012/0095567 | A1 | 4/2012 | Weisman et al. | |
| 2012/0191174 | A1 | 7/2012 | Vinluan et al. | |
| 2013/0268053 | A1 | 10/2013 | Molaei et al. | |
| 2013/0289529 | A1 | 10/2013 | Caira et al. | |
| 2014/0046125 | A1 * | 2/2014 | Gillespie, Jr. ...... | A61B 17/3478 |
| | | | | 600/31 |
| 2014/0046349 | A1 * | 2/2014 | Warner .................. | A61B 17/30 |
| | | | | 606/151 |
| 2014/0188205 | A1 | 7/2014 | Andreas et al. | |
| 2014/0257253 | A1 * | 9/2014 | Jemison ........... | A61B 17/32056 |
| | | | | 606/1 |
| 2014/0257454 | A1 * | 9/2014 | McGee ...................... | A61F 2/82 |
| | | | | 623/1.11 |
| 2014/0371844 | A1 * | 12/2014 | Dale ...................... | A61F 2/2436 |
| | | | | 623/2.11 |
| 2015/0066056 | A1 | 3/2015 | Aquino et al. | |
| 2015/0223953 | A1 | 8/2015 | Pendleton et al. | |
| 2015/0230955 | A1 * | 8/2015 | Farag Eells ............ | A61F 2/954 |
| | | | | 606/108 |
| 2015/0257908 | A1 | 9/2015 | Chao et al. | |
| 2016/0015394 | A1 | 1/2016 | Cedro et al. | |
| 2016/0015507 | A1 | 1/2016 | Johnson et al. | |
| 2016/0242799 | A1 * | 8/2016 | Bonneau .................. | A61B 1/05 |
| 2017/0000598 | A1 | 1/2017 | Bachar | |
| 2017/0049596 | A1 | 2/2017 | Schabert | |
| 2017/0065406 | A1 * | 3/2017 | Calomeni ............ | A61F 2/2436 |
| 2017/0071771 | A1 | 3/2017 | Harada | |
| 2017/0135830 | A1 | 5/2017 | Harkin et al. | |
| 2017/0165064 | A1 * | 6/2017 | Nyuli .................... | A61F 2/2427 |
| 2018/0125516 | A1 * | 5/2018 | Chu .................. | A61B 1/00133 |
| 2018/0185183 | A1 | 7/2018 | Christakis et al. | |
| 2018/0318114 | A1 | 11/2018 | Huang et al. | |
| 2018/0318144 | A1 | 11/2018 | Giovanni et al. | |
| 2019/0038443 | A1 * | 2/2019 | Sicotte ................... | A61F 2/885 |
| 2019/0083261 | A1 * | 3/2019 | Perszyk ............... | A61F 2/2436 |
| 2019/0269510 | A1 | 9/2019 | Zeng et al. | |
| 2019/0282384 | A1 | 9/2019 | Phillips | |
| 2019/0343500 | A1 * | 11/2019 | Damiano .............. | A61M 39/20 |

FOREIGN PATENT DOCUMENTS

| | | | |
|---|---|---|---|
| JP | H06-048674 | U | 7/1994 |
| JP | 2008-515586 | A | 5/2008 |
| JP | 2010-233934 | A | 10/2010 |
| JP | 2014171894 | A | 9/2014 |
| JP | 2018519957 | | 7/2018 |
| JP | 20180524075 | A | 6/2020 |
| KR | 10-1502956 | | 3/2015 |
| WO | 2008086195 | | 7/2008 |
| WO | 2012065625 | A1 | 5/2012 |
| WO | 2013049448 | A1 | 4/2013 |
| WO | 2015111063 | A1 | 7/2015 |
| WO | 2015153507 | | 10/2015 |

(56)            References Cited

FOREIGN PATENT DOCUMENTS

| WO | 2017017499 A1 | 2/2017 |
| WO | 2017081326 A1 | 5/2017 |
| WO | 2017112856 A1 | 6/2017 |

OTHER PUBLICATIONS

International Search Report and Written Opinion in International Patent Application No. PCT/US2020/055067, dated Jan. 29, 2021.
European Search Report in European Patent Application No. 18794309, mailed Dec. 18, 2020.
Search Report from corresponding Japanese Patent Application No. 2019-560245, dated Oct. 15, 2021.
Notice of Reasons for Refusal from corresponding Japanese Patent Application No. 2019-560245, dated Oct. 12, 2021.
Extended European Search Report from European Patent Application No. 20875066.1, dated Oct. 21, 2022.
Office Communication from European Patent Application No. 18794309.7, dated Nov. 23, 2022.
International Preliminary Report on Patentability in International Patent Application No. PCT/US2018/031250, dated Nov. 5, 2019.
International Search Report and Written Opinion in in International Patent Application No. PCT/US2018/031250, dated Jul. 27, 2018.
Instructions for Use: Cordis TrapEase Permanent Vena Cava Filter with the VisEase Angiographic Vessel Dilator, Jan. 2016.
Notification of Reasons for Refusal from corresponding Japanese Patent Application No. 2022-521422 dated Jan. 21, 2025.
First Office Action from related Chinese Patent Application No. 202080070785.3 dated Mar. 30, 2025.
Office Action from corresponding Chinese Patent Application No. 202080070785.3 dated Aug. 15, 2025.

* cited by examiner

DELIVERY SYSTEMS AND DEVICES FOR THE TREATMENT OF BENIGN PROSTATIC HYPERPLASIA AND RELATED LOWER URINARY TRACT SYMPTOMS

RELATED APPLICATIONS

This application claims priority to U.S. Provisional Application No. 62/912,759, filed Oct. 9, 2019. The priority of this application is expressly claimed, and the disclosure is hereby incorporated by reference in its entirety. Further, the application is a continuation-in-part of commonly-owned U.S. application Ser. No. 15/972,031, filed May 4, 2018, the contents of which is also hereby incorporated by reference in its entirety

FIELD OF THE PRESENT DISCLOSURE

This disclosure relates to devices and systems for managing or treating body tissues obstructing a hollow body lumen, such as the prostatic lobe tissues obstructing the urethra.

BACKGROUND

The prostate is a walnut-shaped gland that wraps around the urethra through which urine is expelled from the bladder and plays a crucial role in the reproductive system of men. Although the gland starts out small, it tends to enlarge as a man ages. An excessively enlarged prostate results in a disease known as benign prostatic hyperplasia (BPH). Benign prostatic hyperplasia (BPH) refers to the abnormal, but non-malignant (non-cancerous) growth of the prostate observed very commonly in aging men. BPH is a chronic condition and is associated with the development of urinary outflow obstruction or luminal narrowing in the prostatic urethra. Bladder outlet obstruction (BOO) refers to a blockage at the base of the bladder that reduces or stops the flow of urine into the urethra and may be secondary to BPH. A range of related disorders referred to collectively as Lower Urinary Tract Symptoms (LUTS) can result, including sexual dysfunction, frequent urination, difficulty in voiding urine, urinary retention, urinary leakage, and urinary tract and bladder infections that worsen as the abnormal growth in the prostate enlarges and progresses.

Surgical procedures provide BPH relief by removing a significant portion the prostate tissue. Several traditional surgical procedures are available, all of which require hospitalization and some form of spinal, epidural, or general anesthesia. Transurethral resection of the prostate (TURP) is the main surgical treatment for BPH and remains the gold standard against which other treatments are compared. Traditional surgical techniques differ in the location of the incision made by the surgeon to access the prostate and in the method by which prostatic tissue is removed. For example, some surgeries use laser energy, heat, or radio frequency to remove tissue from the prostate. They include laser enucleation, photoselective vaporization (PVP), transurethral needle ablation (TUNA) using radiofrequency energy, transurethral microwave thermotherapy (TUMT) and transurethral incision of prostate (TUIP). However, these traditional surgical approaches to the treatment of BPH are invasive, non-reversible, and have significant drawbacks including the placement of a temporary catheter for a few months, risk of infection, loss of sexual function, urinary incontinence, and restenosis—wherein recurring hyperplasia of cells in the prostate regrow to cause a recurrence of the narrowing of the urethra opening and also a recurrence of the LUTS symptoms described above.

Although removing prostatic tissue relieves some BPH symptoms, tissue removal by traditional surgical approaches is irreversible and any adverse effects of the surgery may afflict the patient for life or affect the patients' quality of life. Moreover, surgical approaches are associated with the inherent risks from the surgery itself, risk of recurrence from the regrowth of removed prostatic tissue, and, depending on the extent of the disease and the particular surgical approach necessary for an individual patient, can require recovery periods as long as 3 to 6 weeks.

Because of the recognized drawbacks of traditional surgery, less invasive therapies have been developed and, depending on the extent of disease, may be chosen by patients and their physicians as an alternative to lifelong medication or surgery. These less invasive therapies may be suited for those patients not willing or medically not fit to have a surgical procedure performed under general anesthesia. In addition, younger patients also prefer a less invasive, reversible treatment without compromising sexual function, and leave the option of receiving a permanent, non-reversible treatment affecting sexual function at a later age.

Less invasive techniques include transurethral methods that actually remove enlarged prostatic tissue that are generally less traumatic than traditional surgery, but each destroys prostatic tissue and is irreversible. To avoid destroying the prostatic tissue, other therapeutic procedures have been developed that are designed to enlarge the diameter of the prostatic urethra without actual removal of tissue from the prostate gland, such as by implanting a device within the prostatic urethra that is designed to enlarge the diameter of the urethra. A prostatic implant involves a procedure wherein the urologist inserts a small device within the prostatic urethra which is narrowed by enlarged prostatic tissue. Once in place, the implant is designed to expand and help keep the urethra open by pushing out the tissue lobes, while preventing enlarged prostate tissue from total impingement and opening of the urethra. Ideally, prostatic implants eliminate the need to surgically remove prostatic tissue and are expected to reduce the risks of infection, sexual dysfunction, and incontinence, inherent and traditional to even less-invasive, surgical approaches. The procedure may also be designed to be reversible since the implants may be removed and additional surgical treatments may be performed in the future.

It is also desirable to have features on the implant and delivery system for the physician to be able to perform the procedure in an office using standard cystoscopes and common urological techniques used to examine the extent of BPH and obstruction in the prostatic urethra. It is also desirable to reposition the implant in the event that it is mis-deployed. Features to hold the device and reposition the devices, using traditional graspers or other ancillary devices to retrieve stones during urological procedures, in conjunction with imaging using an endoscope or cystoscope are needed. The present disclosure addresses these and other needs.

SUMMARY

This disclosure includes a system for delivering and deploying an implant at a desired location in a lumen of a body. The system has an elongated sheath configured for introduction through a working channel of a cystoscope having an atraumatic tip at a distal end, a handle secured to a proximal end of the elongated sheath, a pusher coaxially disposed within the elongated sheath, a deployment actuator associated with the handle and coupled to the pusher and an implant maintained in a constrained configuration within the elongated sheath adjacent the atraumatic tip, wherein manipulation of the deployment actuator results in relative movement between the pusher and the elongated sheath to cause the implant to be deployed from the atraumatic tip of the elongated sheath.

In one aspect, an advancement knob on the handle is configured to adjust a working length of the elongated sheath.

In one aspect, the deployment actuator is a slider coupled to a proximal end of the pusher. Manipulation of the deployment actuator may retract the elongated sheath to cause the implant to be deployed from the atraumatic tip of the elongated sheath or may move the pusher distally to cause the implant to be deployed from the atraumatic tip of the elongated sheath.

In one aspect, a fluid coupling is associated with the handle and is in fluid communication with a lumen of the pusher configured to conduct irrigation fluid to the atraumatic tip. Continued flow of irrigation fluid is necessary for visualization or imaging during the treatment procedure to deploy the implant in the prostatic urethra. The fluid coupling may be moveable with the deployment actuator.

In one aspect, an implant actuator may be associated with the handle and connected to an implant engaging element, wherein the implant actuator is configured to selectively or gradually release or retract the implant in a controlled way during deployment.

In one aspect, an implant engaging element may be configured to maintain control of the implant during deployment. For example, the implant engaging element may be a preformed shape disposed within the implant that is configured to retard distal movement of the implant when deployed. Alternatively, the implant engaging element may be a releasable tether coupled to a proximal end of the implant. The implant engaging element may also include interlocking features at a distal end of the pusher and a proximal end of the implant. Still further, the implant engaging element may be a wire routed through apertures formed in tissue-engaging portions of the implant that constrains the implant when tensioned or may be a wire routed around tissue-engaging portions of the implant that constrains the implant when tensioned.

This disclosure also includes a device for delivering and deploying an implant at a desired location in a lumen of a body. The device features an elongated sheath configured for introduction through a working channel of a cystoscope having an atraumatic tip at a distal end, a handle secured to a proximal end of the elongated sheath, a pusher coaxially disposed within the elongated sheath and a deployment actuator associated with the handle and coupled to the pusher, wherein manipulation of the deployment actuator results in relative motion between the pusher and the elongated sheath to cause an implant maintained in a constrained configuration within the elongated sheath adjacent the atraumatic tip to be deployed out the atraumatic tip of the elongated sheath.

In one aspect, manipulation of the deployment actuator moves the pusher distally to cause the implant to be deployed from the atraumatic tip of the elongated sheath In one aspect, an advancement knob on the handle may be configured to adjust a working length of the elongated sheath.

In one aspect, a fluid coupling associated with the hand may be in fluid communication with a lumen of the pusher and configured to conduct irrigation fluid to the atraumatic tip. Continued flow of irrigation fluid is necessary for visualization or imaging during the treatment procedure to deploy the implant in the prostatic urethra. The fluid coupling may be moveable with the deployment actuator.

In one aspect, the elongated sheath may be configured to fit within a working channel having an outer diameter not greater than 6 French.

In one aspect, the handle may have a deployment lock that selectively restricts operation of the deployment actuator.

In one aspect, the handle further may have a connector coaxially disposed around the elongated sheath for engaging a lock of the working channel of the cystoscope.

This disclosure also includes a method for delivering and deploying an implant at a desired location in a lumen of a body. The method may involve providing an elongated sheath having an atraumatic distal tip and an implant maintained in a constrained configuration within the elongated sheath adjacent the atraumatic tip, introducing the elongated sheath through a working channel of a cystoscope, positioning the distal tip at target site within the urethra and manipulating a deployment actuator to result in relative motion between a pusher, which is coaxially disposed within the elongated sheath, and the elongated sheath to deploy the implant from the atraumatic tip of the elongated sheath.

In one aspect, a working length of the elongated sheath may be adjusted before deployment of the implant.

In one aspect, an implant actuator may be manipulated to maintain control of the implant during deployment. Such control may include partial deployment of the implant or retraction of the implant. Such control may also include rotation and placement of the implant for optimal positioning to push the prostatic lobes and create the opening any time during deployment, prior to releasing the implant.

In one aspect, an implant actuator may be manipulated to release the implant after being driven distally out the sheath.

In one aspect, implant length may be determined by employing a balloon catheter.

In one aspect, implant length may be determined by employing a laser marker catheter.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
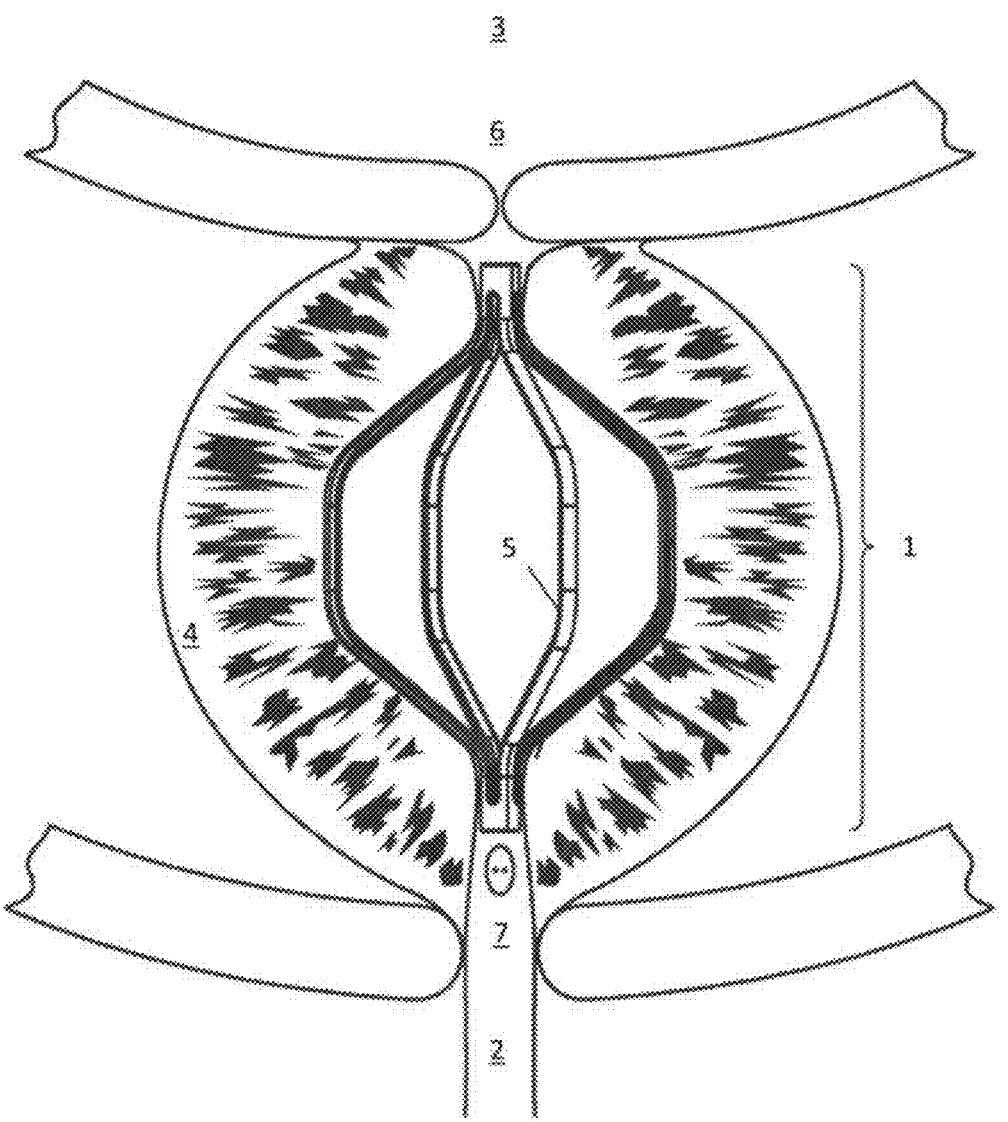
FIG. 1 is a cross-section of the male anatomy comprising the lower portion of the bladder, and the prostatic urethra in a physiological configuration typical of a patient suffering from BPH, showing placement of an implant that may be disposed using the devices and systems of this disclosure in the prostatic urethra and engaging prostatic tissue on either side thereof between the bladder neck opening and the verumontanum according to an embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. Moreover, as used in this specification and the appended claims, the singular forms "a, "an" and "the" include plural referents unless the content clearly dictates otherwise.

Definitions: The terms "therapeutically effective displacement" or "therapeutically effective retraction" or "therapeutically effective expansion", are used interchangeably herein and refer to an amount of displacement of prostatic tissue proximate to a restricted area of a urethra sufficient to increase the urethral lumen and treat, ameliorate, or prevent the symptoms of benign prostatic hyperplasia (BPH) or comorbid diseases or conditions, including lower urinary tract symptoms (LUTS), bladder outlet obstruction (BOO), benign prostatic obstruction (BPO), wherein the displacement of prostatic tissues exhibits a detectable therapeutic, prophylactic, or inhibitory effect. The effect can be detected by, for example, an improvement in clinical condition, or reduction in symptoms or absence of co-morbidities. Examples of clinical measures include a decrease in the international prostate symptom score (IPSS), reduction in post-void residual (PVR) volume of urine in the bladder after relief or increase in the maximum urinary flow rate (Qmax) or improvement in quality of life (QoL), improvement in sexual health (sexual health inventory for men or SHIM score, men's sexual health questionnaire or MSHQ score) after treatment. The precise distance or volume of the displacement of prostatic tissue will depend upon the subject's body weight, size, and health; the nature and extent of the enlarged or diseased prostatic condition and the size of the implant selected for placement in the patient.

As used herein, a patient "in need of treatment for BPH" is a patient who would benefit from a reduction in the presence of or resulting symptoms of enlarged prostatic tissue caused by a non-malignant enlarging of the prostate gland and related disorders, including LUTS, urinary outflow obstruction symptoms and luminal narrowing of the prostatic urethra. As used herein, the terms "implant" or "expander" or "device" refer to the prosthetic device that is implanted within the prostatic urethra to relieve LUTS associated or caused by BPH.

As used herein, the terms "tissue engaging" with regard to arms, struts or other extensions of the structure of the implant refers to a length of the physical structure of the implant that engages prostatic tissue along the main portion of the lobes of the organ compressing on the urethra and restraints the tissue from further impingement on the patency of the urethra. "Tissue retracting" refers to the ability of the structure of the implant to exert the requisite force to displace tissue away from the compressed or narrowed urethra. The requisite force could be supplied by the inherent structure of the implant or by the expansion of the implant from the compressed to the expanded configuration, particularly where the implant is fabricated from a shape-memory or super-elastic material having a predetermined expanded configuration designed to engage the hyperplasic prostate tissue and exert the requisite tissue retraction force. The length of a tissue-engaging or tissue-retracting structural feature in contact within these definitions is spaced away from the intra-lobular grooves that run along the length of the prostate surrounding the urethra and requires contact with a length of tissue along the length of the two lateral or lateral and medial lobes.

With respect to orientation of the various structures and anatomical references described herein, the term "proximal"

and "distal" are relative to the perspective of the medical professional, such as an urologist, who is manipulating the delivery system of the disclosure to deploy the implants described herein. Accordingly, those features of the delivery system held by the hand of the urologist are at the "proximal" end and the assembled system and the implant, initially in its compressed configuration, is located at the "distal" end of the delivery system.

Referring to FIG. 1, a cross-section of the male anatomy shows the prostate gland 1 surrounding the urethra 2. The urethra 2, under normal conditions, provides fluid communication from urine stored in the bladder 3 to be expelled from the body under voluntary muscular control of the external urethral sphincter. Normal or "true" prostate tissue 4 surrounds the urethra 2 and, in the absence of disease, does not impinge on the patency of the urethra 2. In patients suffering from benign prostatic hyperplasia (BPH), the urethra 2 is narrowed by hyperplasic tissue, i.e. prostate tissue 4 that exhibits excess growth towards the urethra 2. This excess of non-cancerous cellular growth leads to the symptoms of BPH described above, including, lower urinary tract symptoms (LUTS) and urinary outflow obstruction, and urinary incontinence. In FIG. 1, an implant 5 delivered using the devices and systems of this disclosure is shown engaging prostate tissue 4 along a length of the implant 5 to restore the patency of the urethra 2 and to permit unimpeded urine flow from the bladder 3. The selective placement of the implant 5 at a target site, between bladder neck opening 6 and verumontanum 7, as shown is an important characteristic so that implant 5 does not puncture, perforate or incise the surrounding tissue. The implant 5 is designed to remain in place within the prostatic urethra 2. The implant 5 does not extend into the urinary bladder 3, where the structural material of the implant 5 could become encrusted or otherwise degraded from constant exposure to urine causing complications and making retrieval more difficult, and the implant 5 does not interfere with the voluntary control of the external urethral sphincter or interfere with sexual functions.

An implant 5 according to the techniques of this disclosure has a plurality of tissue-engaging structures to exert a force against enlarged prostatic tissue 4 proximate to the urethra 2. As described below, the number of the plurality of tissue-engaging structures can be 2, 4, or greater than 4 tissue-engaging extensions, such as struts or arms. The use of 3 extensions is avoided when the three extensions are oriented to each fit within the intralobular grooves of the prostate. Accordingly, any plurality of tissue engaging structures is a possibility as long as the structure is oriented asymmetrically to ensure that the implant 5 is oriented outside the 3 intralobular grooves formed by the length of tissue contact between the 2 lateral and one medial lobes. Embodiments using three tissue-engaging structures may be used to treat anatomies when the urethral anatomy consists of bilateral lobes and the third lobe is not involved with urethral narrowing.

The implants 5 may be fabricated from shape memory materials, alloys, spring materials, and super elastic materials including Nitinol (nickel-titanium alloy), Nitinol-based alloys, cobalt chromium alloys, spring steels, and spring stainless steels. Other known shape memory materials include poly-ether-ether-ketone (PEEK), and shape memory and bio-absorbable polymers and metals (polylactic acid, polyglycolic acid and their copolymers; magnesium alloys). The above materials may be coated with thin film coatings to prevent encrustation, corrosion and stone formation. Coatings may include ceramic materials like alumina, silicon carbide, silicon nitride and zirconia and other ceramic coatings that are inert to urine and prevent encrustation, stone formation and to prevent the deterioration of the material forming the implant in the chemical or urine environment. Coatings may also be polymers such as polytetrafluoroethylene (PTFE), Parylene, silver and other antimicrobial coatings, silicone derivatives, and other similar materials recognized by those of ordinary skill in the art.

The implant 5 may also include therapeutic coatings adhered to the surface of the implant 5 for controlled drug release following implantation in the prostatic urethra 2 in the manner known for drug-eluting implants to reduce hyperplasia and tissue proliferation. The coatings contain pharmaceutically active anti-inflammatory drugs and anti-proliferative agents including sirolimus, novolimus, everolimus, biolimus, zotarolimus, paclitaxel and others that are used to prevent restenosis.

Implants 5 may also be coated with drugs to treat BPH symptoms. Such embodiments have the advantage of using high locally high tissue doses in the diseased prostatic regions of the urethra 2 for greater effectiveness to relax smooth muscle cells, reduce tissue proliferation and size of the prostate without incurring the side effects from drugs circulating in other parts of the body. Potential drug candidates include alpha-adrenergic blockers like, alfuzosin, doxazosin, tamsulosin, terazosin and silodosin. Other drug candidates include 5-alpha-reductase inhibitors like, dutasteride and finasteride, and anticholinergic agents. Other drug candidates are anti-cholinergic agents like, oxybutynin, fesoterodine, darifenacin, tolterodine tartrate, tolterodine, solifenacin. A combination of drugs may also be coated on the surface, including alpha blocker+5-alpha-reductase inhibitor or alpha blocker+anticholinergic agents. In addition, anti-infective agents or antimicrobial agents or antibiotics like fluoroquinolones (e.g., ciprofloxacin) macrolides, tetracyclines, and trimethoprim.

Typically, the drugs are mixed with solvents and polymers into solution and spray coated on the outer surface of the implant 5 to achieve the desired drug release characteristics. The manufacturing processes are similar to those used for drug eluting stents used to treat coronary artery disease. Often, the coating may be on the abluminal side to ensure more effective drug release and deposition into the urethral tissue of the prostatic urethra 2 and minimize washout during urine outflow. The drugs may also be deposited in micro-reservoirs or micro-depots on the outer surface of the implant 5 to load the drug and covered by a polymeric coating to controllably elute drug into the urethral tissue. Typical polymers used to load the drugs are polylactic acid (PLA), poly-L-lactic acid (PLLA) polyglycolic acid (PGA), and their copolymers; polyurethanes; poly(methyl methacrylate) (PMMA) or poly(n-butyl methacrylate) (PBMA); and their combinations thereof. Other polymers and solvents may be used by those skilled in the art to load sufficient drug and maintain coating integrity with the implant surface. Multiple layers of coatings may be used to achieve the desired drug loading and controlled release characteristics.

Figures 2A, 2B:
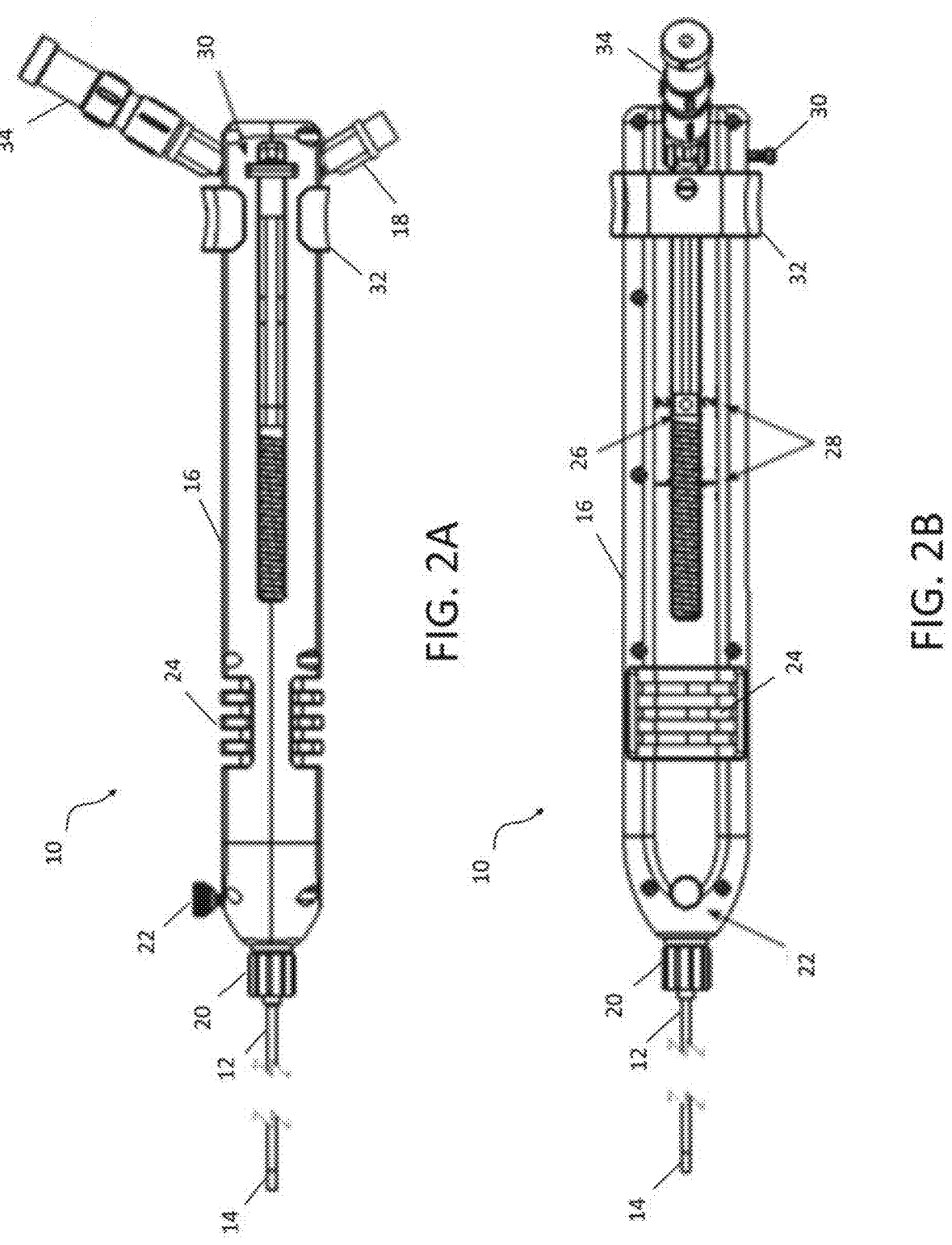
FIGS. 2A and B schematically depict top and side views of a system for deploying an implant according to an embodiment.

According to the techniques of this disclosure, the implant 5 for restoring patency of the urethra 2 is delivered using a system that is designed to be compatible with commercially-available or standard flexible cystoscopes. Specifically, the system is designed to advance through the working channels of flexible cystoscopes, which have inner lumen diameters between 6-9F or 2-3 mm. Referring to FIGS. 2A and 2B, side and top views of delivery system 10 are shown respectively. Implant 5, not shown in these views, is held in a constrained configuration within an elongated, hollow delivery tube, delivery catheter or delivery sheath 12 adjacent to the soft and atraumatic distal tip 14. The catheter or sheath 12 may be made from a thin-walled polymeric tube with sufficient strength to constrain the implant 5, while also having the flexibility and sufficient torquability to navigate tortuous anatomy and assist advancement to the prostatic urethra 2. In addition the tubular sheath 12 or catheter may be reinforced with a metallic wire coil or metallic wire braid to achieve desired performance characteristics of strength, flexibility, low profile, torquability, flexibility and pushability to advance the delivery system 10 containing the implant 5 to the target site. The terms delivery sheath 12, delivery catheter and delivery catheter tube may be used interchangeably throughout the document. The delivery sheath 12 may also have differential wall thickness or stiffness on the distal end, where the implant 5 is constrained to further improve flexibility of the system (sheath plus implant). In other embodiments, the catheter may have marker bands (with different colors) at the distal end to denote the location of the implant 5 with the delivery sheath 12 and the position of the catheter relative to distal end of the cystoscope or exit point of the working channel of the cystoscope. In other embodiments, the distal tip of the catheter may be softer and flexible compared to the hardness or stiffness of the shaft body to cause less trauma to the urethra 2 wall. Such soft atraumatic tip distances may be 0.5-10 mm long, or more preferably 1-2 mm. The proximal end of sheath 12 is connected to handle 16, which features an irrigation port 18 for delivery of saline irrigation to allow imaging, a cystoscope locking luer 20 that locks and securely attaches the delivery system 10 to the luer connector on flexible cystoscopes allowing one handed delivery system operation by the physician and a rotation locking knob 22 to prevent rotation of the delivery handle/ system during the deployment or treatment procedure. For example, knob 22 may comprise a screw that when tightened, engages with the luer connector hub 60 to prevent it from rotating. Handle 16 also has a catheter advancement knob 24 which is rotated to change the working length of the delivery system 10 to accommodate various scope working lengths and adjust the position of the tip of the delivery sheath 12 and accurately position the device at the target site. Catheter position indicator 26 provides visual feedback of the length adjustment in conjunction with reference catheter position markers 28. Deployment safety lock 30 is configured to prevent premature deployment of the implant 5 by restricting movement of a deployment actuator, such as slider 32 in this embodiment, which when pushed deploys the implant 5 at the target site. An implant engaging element 46 configured to assist accurate placement of the implant 5 as discussed below (not shown in this view), such as a capture wire, is coupled to implant actuator 34, so that manipulation releases the implant 5 during deployment as discussed in further detail below. In other embodiments, implant actuator 34 and the associated mechanisms may be omitted.

As noted, distal tip 14 of delivery system 10 is soft and atraumatic. A color differential between the distal tip and a shaft of delivery catheter 12 may be employed to provide a visual indication of a specified distance, to assist deployment of the implant 5 at the target site or a few millimeters away from the desired anatomical location. In one embodiment, the distal 5 mm at the tip 14 is colored white compared to the blue shaft to assist placement of the implant 5 5 mm from the verumontanum within the prostatic urethra 2. The distal tip 14 may also be made radiopaque using special materials (polymers containing barium sulfate) to assist placement under x-ray fluoroscopy. The distal tip 14 may be straight or curved to cause minimal damage to the urethral wall.

Elongated delivery sheath 12 is flexible and compatible with steerable cystoscopes commonly used by urologists for the diagnosis and treatment of chronic conditions and symptoms related to the urinary 2 and reproductive system. Disposing the implant 5 within sheath 12 holds it in a constrained state, at the distal end, such that implant 5 may be passed through a much smaller lumen before it is expanded. Irrigation is also passed through sheath 12 to keep the camera or imaging view clear of cloudiness and debris. Sheath 12 may have a hydrophilic coating to improve lubricity during advancement or may be uncoated. Further, sheath 12 may have more than one lumen for different functions (irrigation flow lumen, implant engagement element, deployment mechanism, light source, imaging elements and others). It may have a preset shape and stiffness to displace prostatic and/or conform to the anatomy and enable it to be steerable or advance to the target site.

Figure 3:
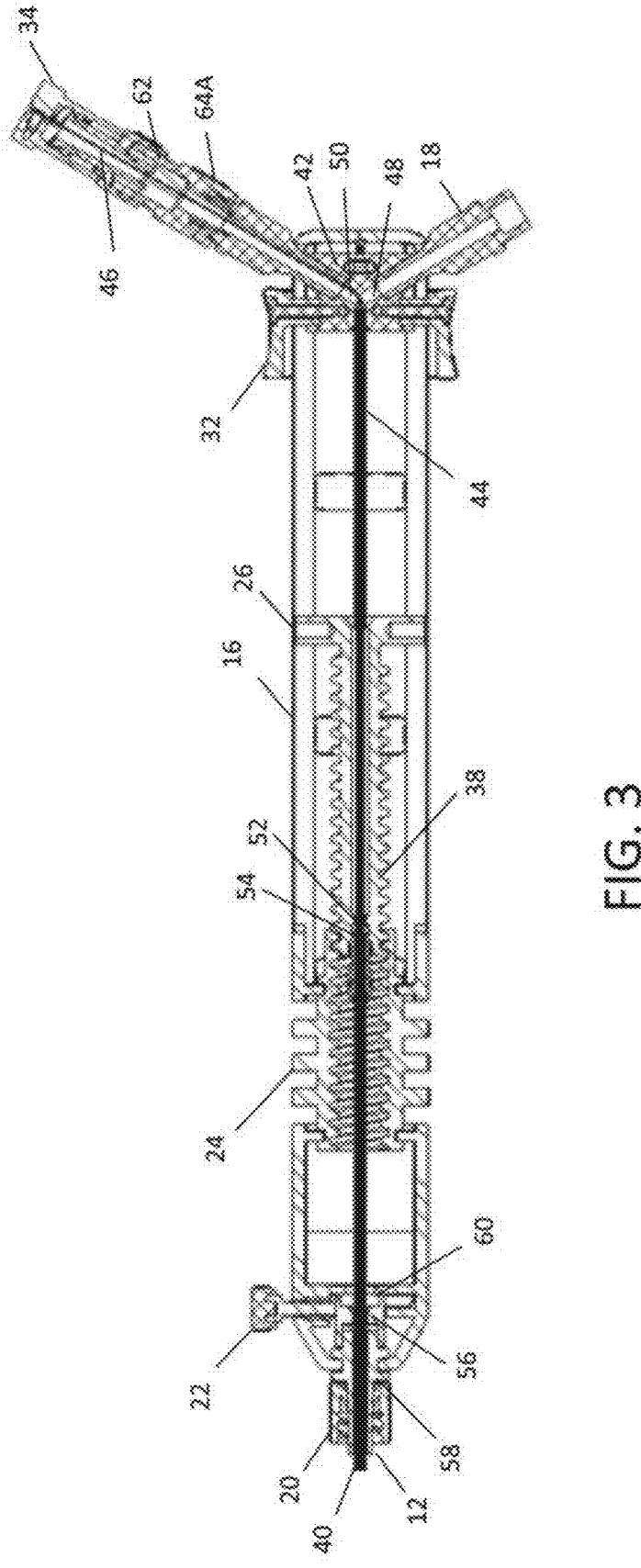
FIG. 3 schematically depicts a cross-sectional view of the deployment system according to an embodiment.

Further details of delivery system 10 are shown in the cross-sectional view of FIG. 3. In particular, catheter advancement knob 24 is coupled to catheter advancement screw 38 via a locking thread. When knob 24 is rotated, the thread translates rotation into linear motion and adjusts the working length of the delivery system 10, i.e. the length of delivery catheter 12 exposed from the handle 16. Employing locking thread ensures that the delivery catheter or sheath 12 position is fixed when the user activates deployment actuator, i.e. slider 32 and is unaffected by the deployment motion. The external threads of screw 38 mate with knob 24 to adjust the working length of sheath 12. Disposed within the lumen of sheath 12 is pusher tube 40, with its proximal end coupled to slider 32. Slider 32 also actuates moveable fluid coupling 42. Lock rod 44 has selectable engagement with deployment safety lock 30 so that when engaged, the relative distance between moveable fluid coupling 42 and catheter advancement screw 38 is maintained. Further, slider 32 is prevented from displacing pusher tube 40 and prematurely or accidently deploying the implant 5 during pre-procedure handling. When deployment is desired, withdrawing lock 30 allows slider 32 to advance and drive pusher tube 40 distally, thereby pushing the implant 5 out the distal end of sheath 12 to cause deployment at the target site. Movable fluid coupling 42 provides two pathways that are joined in communication with pusher tube 40 to allow for saline irrigation through irrigation port 18 and a lumen for implant engaging element 46, such as a capture wire as noted above, which is controlled by implant actuator 34. Irrigation fluid enters through irrigation port 18 and lumen 48 while implant engaging element 46 is routed through lumen 50 before they join and continue through the lumen of pusher tube 40. The pusher tube 40 may be hollow or solid tube depending on the desired performance characteristics of pushability (to push the implant 5 and deploy at the target site) and provide additional irrigation and increase the fluid coupling area to enhance imaging during cystoscopy.

Pusher seal 52 is compressed between catheter advancement screw 38 and catheter hub 54 to prevent fluid leakage between the inner diameter of sheath 12 and the outer diameter of pusher tube 40. Likewise, catheter seal 56 is compressed between luer connector 58 and luer connector hub 60 to prevent fluid leakage between the cystoscope working channel and the outer diameter of sheath 12. Thus, when rotation locking knob 22 is tightened against luer connector hub 60, handle 16 is unable to rotate relative to the cystoscope. Other embodiments for deploying the expander implant 5 may be designed to include mechanisms where the pusher tube is stationary and locked to the handle 16 and the implant engaging element 46. Sliding or moving the implant actuator may retract the sheath 12 to expose the implant 5 and deploy the expander implant 5 in the prostatic urethra 2.

Implant engaging element 46 is connected to implant actuator 34 via implant actuator seal 62 housed inside body 64A, so that implant actuator seal 62 and implant actuator 34 prevent irrigation fluid from exiting out through lumen 50. Slider 32 is connected to movable fluid coupling 42 as described, so that the coupling 42 moves along with the slider 32 during implant deployment, thereby providing continuous irrigation and imaging of anatomical landmarks during the treatment procedure. Implant actuator 34 is disconnected from body 64A and implant engaging element 46 is withdrawn after implant deployment at the target site, detaching the implant 5 from delivery system 10. Advantageously, implant actuator 34 may facilitate an incremental and well-controlled deployment of implant 5, so that the implant 5 does not "spring open" or "spring forward" prematurely and deploy at in an unsuitable configuration or location away from the target site. By maintaining control over implant 5 even after expansion, premature deployment or misplacement is reduced.

Movable fluid coupling 42 serves multiple functions, including coupling slider 32 to pusher tube 40 for deployment of the implant 5, providing fluid communication between irrigation port 18 and pusher tube 40 through lumen 48, maintaining clear visualization for video by flushing and enabling the connection of the various components noted above associated with slider 32 during deployment of the implant 5. Moreover, movable fluid coupling 42 cooperates with lock rod 44 and lock 30 to provide the functionality discussed above. Movable fluid coupling 42 also provides lumen 50 for implant engaging element 46 that is coupled to implant actuator 34. When lock 30 is disengaged, movable fluid coupling 42 is allowed to translate distally towards catheter advancement screw 38 when the user advances slider 32.

Figure 4:
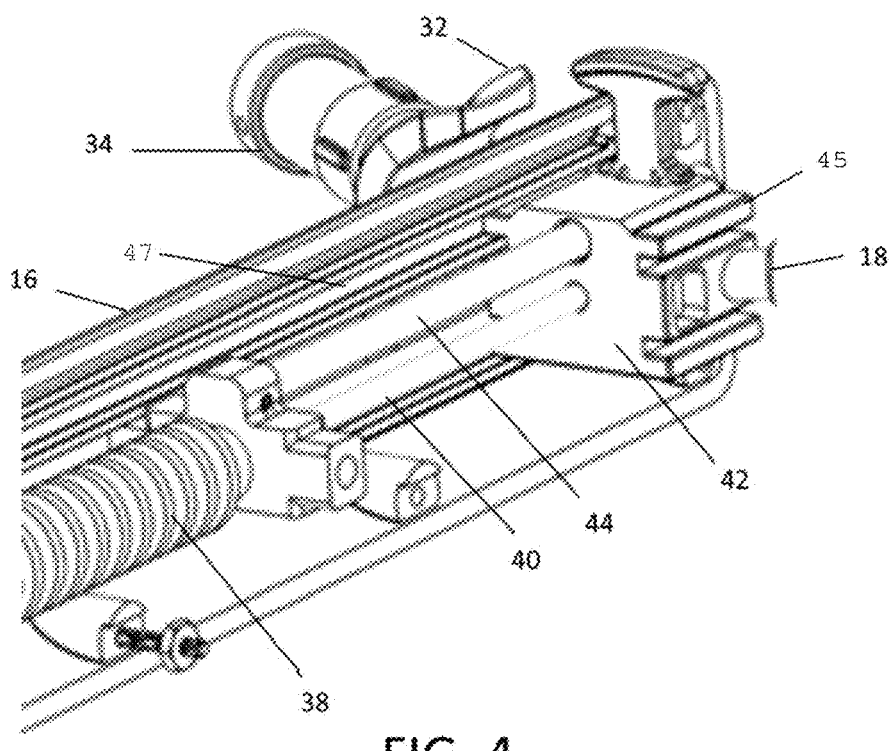
FIG. 4 schematically depicts a detail view of a moveable fluid coupling of the deployment system according to an embodiment.

As shown in the detail view of FIG. 4, movable fluid coupling 42 has a defined path guided by grooves 45 that mate with rails 47 in handle 16. Advancing slider 32 translates movable fluid coupling 42 distally, along with pusher tube 40 to deploy the implant 5 out of the distal tip of sheath 12.

Irrigation port 18 allows the connection of irrigation via common luer lock connector. It may also be used to deliver therapeutic agents to the treatment site. There may be another port that provides a lumen for aspiration or a suction, to facilitate transport of tissue or fluid out of the target site or patient. The suction source may be gravity, a powered vacuum pump, a wall suction outlet, or a syringe, for example.

Pusher tube 40 is a separate flexible member inside sheath 12 that is used primarily to eject or push the implant 5 from delivery system 10, thereby deploying the implant 5 at a desired target site. Suitable materials include PEEK (polyether-ether-ketone), other polymers or spring materials, and super elastic materials including Nitinol (nickel-titanium alloy), Nitinol-based alloys, cobalt chromium alloys, spring steels, and spring stainless steels that have sufficient strength, flexibility and pushability to deploy or retract the implant 5 from the delivery system 10 without kinking. Pusher tube 40 also provides a lumen for irrigation as discussed above to provide fluid flush to maintain clear visualization from the video camera. Pusher tube 40 is coaxially disposed within sheath 12.

Figure 5:
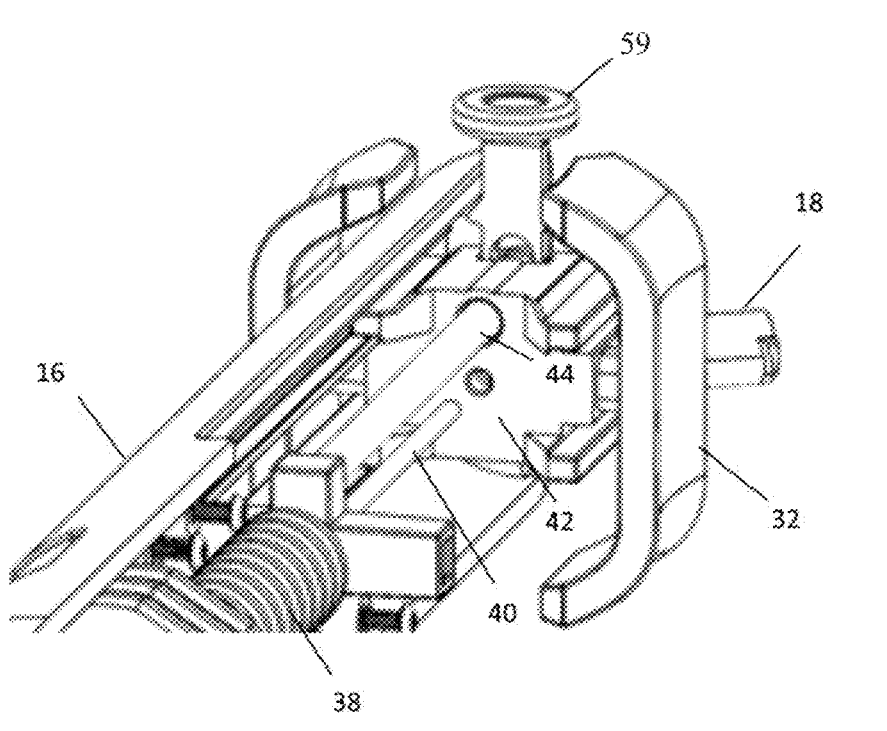
FIG. 5 schematically depicts a detail view of an alternative deployment lock of the deployment system according to an embodiment.

In alternative embodiments, the safety lock function can be implemented with a push actuation as opposed to pulling. For example, FIG. 5 shows a detail view in which similar elements have the same reference numbers. Here, when lock button 59 is depressed, a wider aperture is centered around lock rod 44, allowing movable fluid coupling 42 to translate distally under control of slider 32.

Figure 8A:
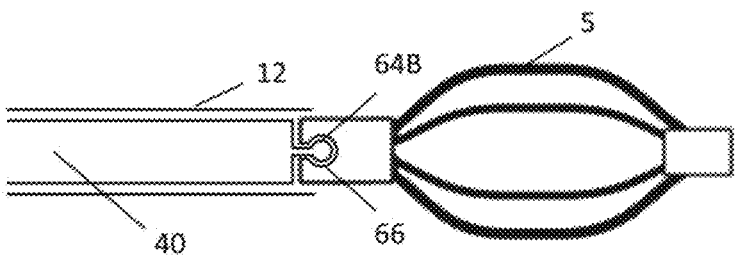
FIGS. 8A-C schematically depict an interlocking implant engaging element according to various embodiments.
Figure 8B:
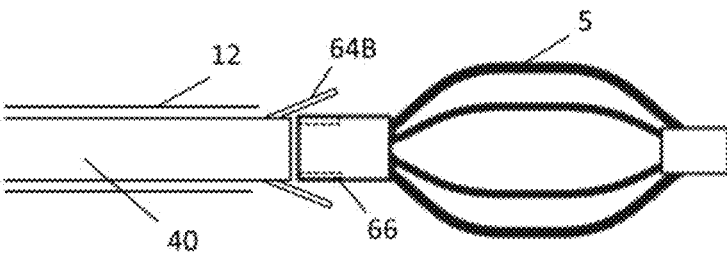
Figure 8C:
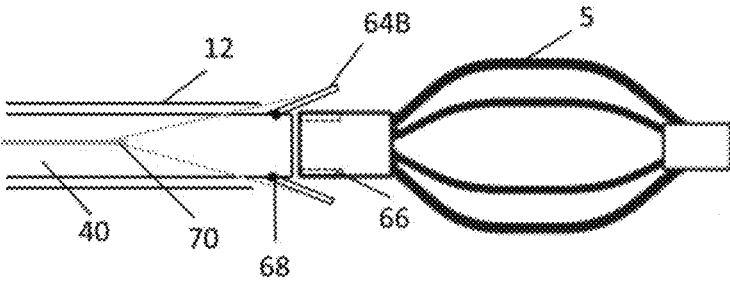
Figure 14:
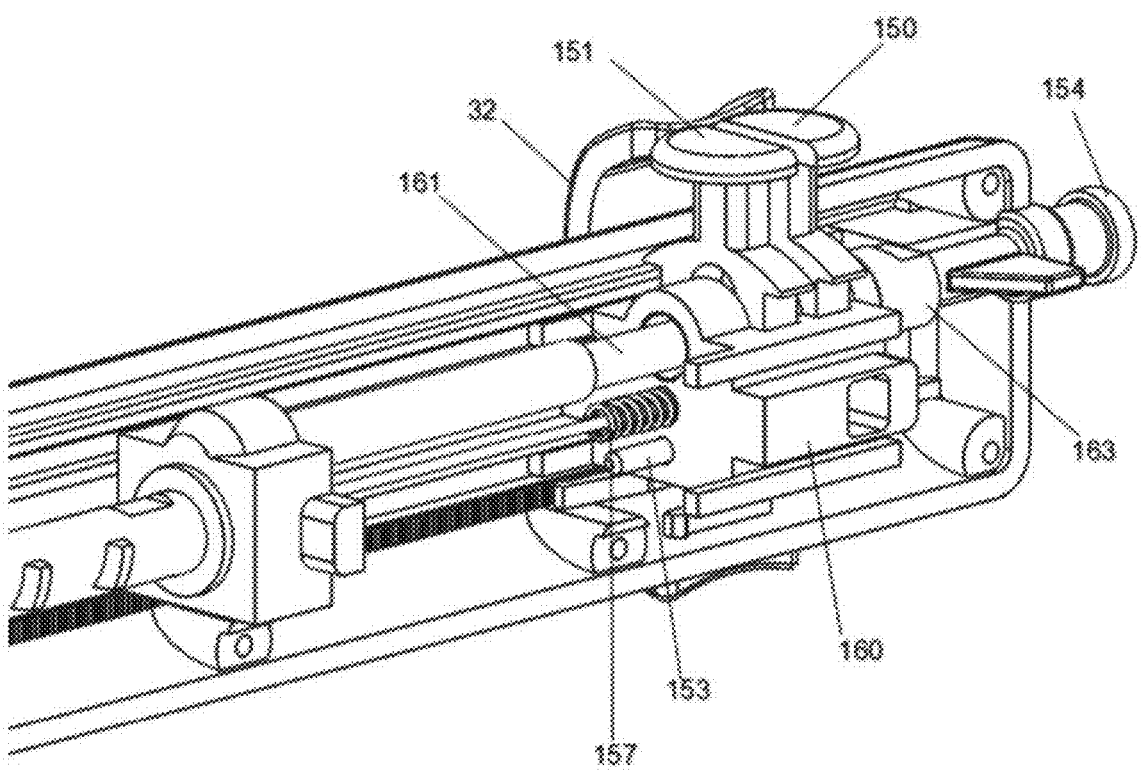
FIG. 14 schematically depicts a detail view of an alternative deployment system according to an embodiment, with an alternative deployment safety lock and irrigation coupling without implant actuator.
Figure 15:
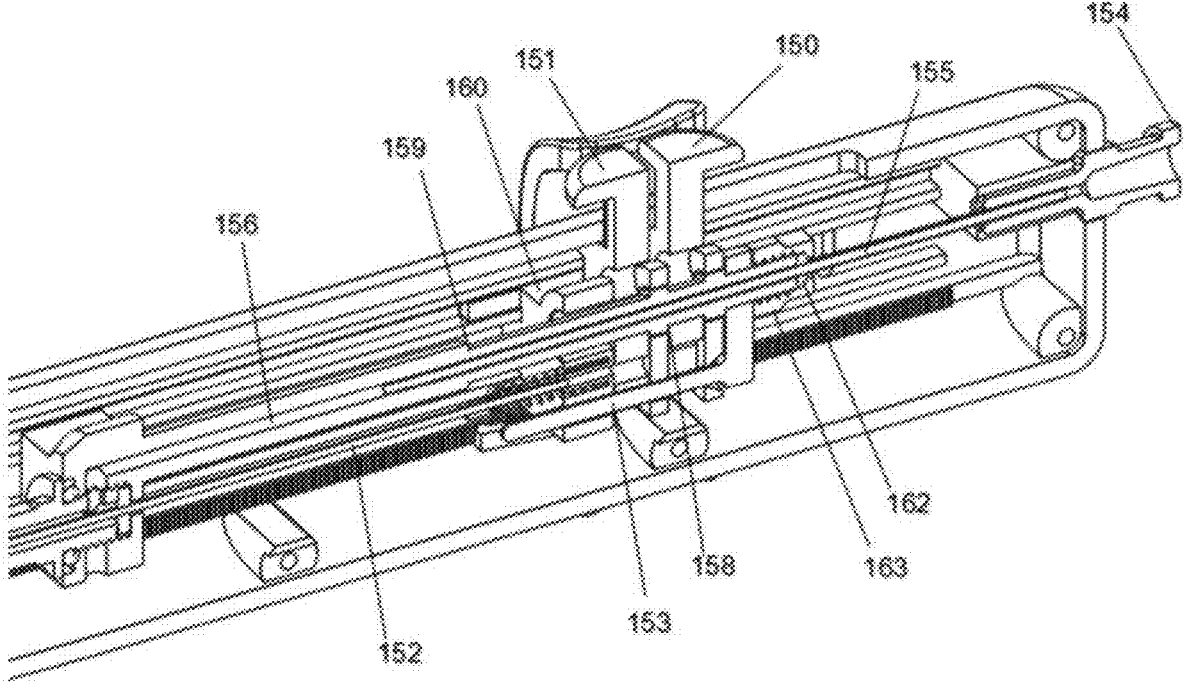
FIG. 15 schematically depicts a detail view of an alternative deployment system according to an embodiment, with an alternative deployment safety lock and irrigation coupling without implant actuator.

In another embodiment there are two push safety locks that allow a partial deployment of implant 5 prior to full deployment. For example, FIG. 14 and FIG. 15 show disposed within the lumen of sheath 12 is pusher tube or pusher rod or pusher wire 152, with its proximal end coupled to pusher block 160. Slider 32 actuates moveable pusher block 160. Deployment track 161 has selectable engagement with deployment safety lock 150 and 151 so that when engaged, the relative distance between pusher block 160 and catheter advancement screw 38 is maintained. Further, slider 32 is prevented from displacing pusher tube 152 prematurely or accidently deploying the implant 5 during pre-procedure handling. Initially, lock 151 is unable to be depressed due to interference with auto-lock 153 and lock 150 is in contact with stop 158. When deployment is desired, depressing lock 150 allows pusher block 160 to advance and drive pusher tube 152 distally until lock 151 contacts stop 159 wherein implant 5 is partially deployed from the sheath 12 allowing the orientation and position of the implant 5 to be viewed prior to releasing the implant 5 and complete deployment. When lock 151 is in contact with stop 159, lock 151 can be depressed allowing pusher block 160 and pusher tube 152 to translate further distally thereby deploying the implant 5 fully out the distal end of sheath 12 at the target site. Spring 157 returns the pusher block 160 and pusher tube 152 proximally thus re-constraining projections 64B (as shown in FIG. 8A to 8C) into the constraint of sheath 12 to prevent injury to the urethra and damage to the cystoscope during withdrawal of delivery system 10. Irrigation fluid enters through irrigation port 154 and irrigation tube 155. Moveable deployment track 161 provides a fluid path 156 that telescopes over the fixed irrigation tube 155. Irrigation seal 162 is compressed between deployment track 161 and seal nut 163 to prevent fluid leakage between the inner diameter of deployment track 161 and the outer diameter of irrigation tube 155. One exemplary method for employing delivery system 10 is as follows. Once the subject is diagnosed for BPH/LUTS using transrectal or transabdominal ultrasound, an appropriate delivery system 10 containing an implant 5 of sufficient length to treat the prostatic urethra length is selected. In addition, a cystoscopy may be performed to further verify the target length of treatment in the prostatic urethra 2. Typically, the treatment length is taken as the length from the bladder neck to the verumontanum. The implant 5 is desirably placed between the bladder neck 6 and the verumontanum 7. In some cases, the implant 5 may be placed between the bladder neck 6 and the external sphincter. First, a flexible cystoscope is inserted through the urinary tract to reach the prostatic urethra 2, and the target prostatic urethra 2 treatment length is measured. The cystoscope tip is positioned near the verumontanum 7. Delivery system 10 with an implant 5 of appropriate length is selected. Catheter shaft length is adjusted using catheter advancement knob 24. Catheter position indicator 26 is aligned with the appropriate catheter position marker 28. Saline bags and connector tubes are disconnected from the cystoscope and connected to irrigation port 18 of delivery system 10 to allow saline irrigation. Sheath 12 is introduced through the cystoscope's instrument channel and cystoscope locking luer 20 on handle 16 is locked to the luer connector of the cystoscope by rotating it in the clockwise direction. Handle 16 is then rotated to a desired position and locked engaging rotation locking knob 22. Sheath 12 is further advanced using catheter advancement knob 24, until the white distal marker at distal tip 14 of sheath 12 appears within the field of view of the cystoscope. Once the target site for implant 5 deployment is confirmed, the deployment safety lock 30 is disengaged by pulling it perpendicularly away from handle 16. While holding the cystoscope in a fixed position, implant 5 is deployed at the target site by slowly advancing deployment slider 32 distally along the handle 16. The implant 5 may be partially deployed to verify the position and then retracted to reposition and deploy at the desired location. The implant 5 orientation may be controlled by rotating the delivery catheter or delivery sheath when the implant 5 is partially deployed. The opening in the prostatic urethra 2 may be verified by completely deploying the implant 5, but not releasing from the implant engaging element 46. If an alternate or better implant 5 orientation relative to the prostatic tissue lobes or position relative to the bladder neck 6 or verumontanum 7 is desired, the implant 5 may be retracted into the sheath 12, repositioned or re-oriented and then deployed at the desired location. Once the implant 5 is deployed at the target site, the implant actuator 34 is manipulated, such as by unscrewing to disengage implant engaging element 46. In some embodiments, such as those employing a capture wire, this corresponds to retracting implant engaging element 46 a minimum distance (e.g., 6 cm) to disengage delivery system 10 from implant 5. Finally, handle 16 is unlocked from the cystoscope by freeing cystoscope locking luer 20 and system 10 is retracted from the instrument channel of the cystoscope.

In other embodiments, delivery system 10 may be adapted to incorporate light-source and image-capture elements to obviate the need for compatibility with commercially available flexible cystoscopes. There are several advantages for using such modifications to deploy the implant 5 at the target site. First, it can reduce the profile (or outer diameter) of the delivery system 10 to be introduced into the urethra 2. Smaller profile systems are more flexible, less traumatic and induce less pain. Second, the delivery systems 10 of this disclosure are capable of incorporating and delivering more implant 5 designs (collapsed to a larger constrained diameter), without constraints imposed by the working channels of existing delivery systems. Third, the delivery system 10 can be a disposable medical device without the need for using expensive cystoscopes that need to be resterilized and periodically refurbished and avoid the risks associated with resterilization. Such embodiments include the aspects discussed above, together with actuating/articulating elements to allow navigation and visualization, a video connector for interfacing to standard VGA, smart phone or tablet displays, a catheter shaft having an increased lumen for improved irrigation and connector cabling for light source and image capturing, and the distal tip correspondingly includes a light source, a camera and a combined irrigation and implant exit.

Figure 6:
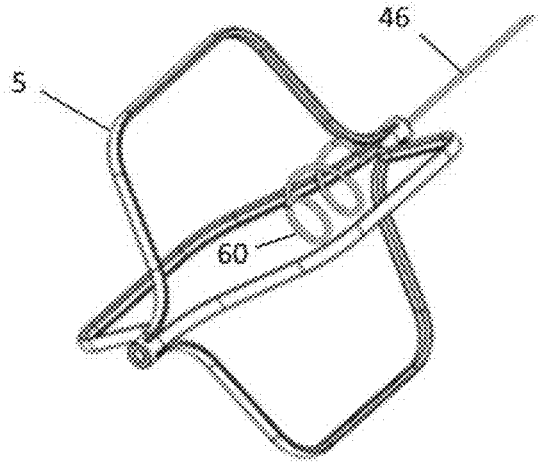
FIG. 6 schematically depicts an implant engaging element having a preformed shape according to an embodiment.

Turning now to FIG. 6, an exemplary embodiment of implant 5 is shown in conjunction with implant engaging element 46. As can be seen, implant engaging element 46 comprises a preformed wire 60 at the distal end that is configured to retard the release of implant 5 during deployment to facilitate more accurate placement. In other embodiments, implant engaging element 46 may be a threaded rod or tube that screws onto implant 5 or a tube or rod or tube with a feature that interlocks with a feature on implant 5 to allow for controlled release during deployment. Further, implant engaging element 46 may also be a braided or monofilament thread, line, suture or wire that functions in a similar manner to temporarily restrain implant 5 during deployment.

Figures 7A, 7B, 7C:
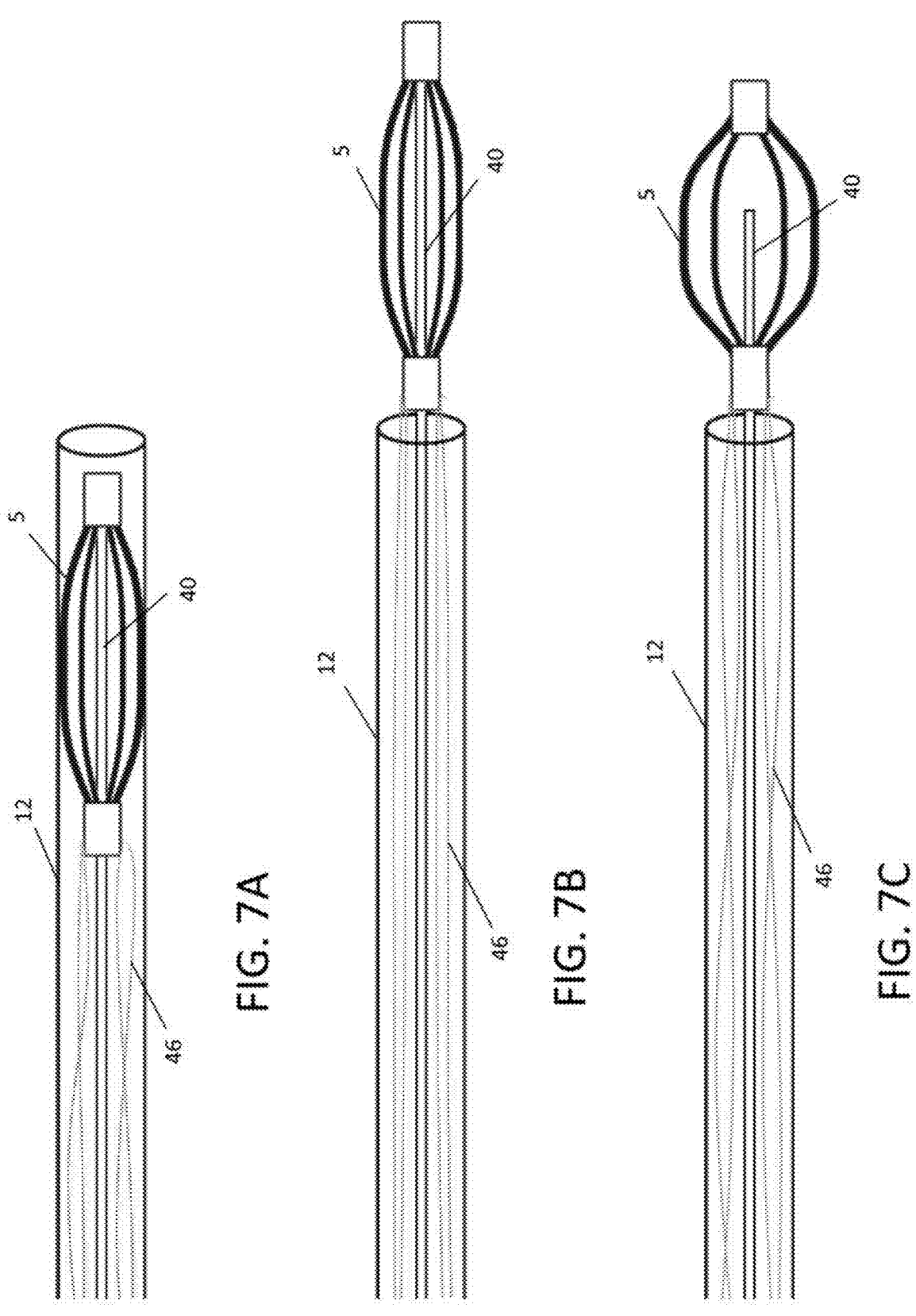
FIGS. 7A-C schematically depict usage of tether loops as an implant engaging element according to an embodiment.

Another aspect of the techniques of this disclosure is illustrated in FIGS. 7A-7C which show the cooperation between pusher tube 40 and implant engaging element 46 when deploying implant 5. First, FIG. 7A shows implant 5 in its constrained configuration disposed within the distal end of sheath 12. Pusher tube 40 engages a distal feature of implant 5, such as an arm or hub, so that distal movement of pusher tube 40 ejects implant from sheath 12. Implant engaging element 46 comprises tether loops that are coupled to a proximal portion of implant 5. In this state, the tether loops are substantially slack. As implant 5 is deployed by distal motion of pusher tube 40 as shown in FIG. 7B, tension can be applied to implant engaging element 46 in opposition to the force applied by pusher tube 40 to control the rate of deployment, prevent implant 5 from jumping away from the desired position and help keep implant 5 in its constrained configuration. Once implant 5 is in its desired location, pusher tube 40 can be withdrawn proximally and/or implant engaging element 46 can be slackened, allowing the resilience of implant 5 to cause expansion to the configuration that maintains patency of the urethra 2. Once deployed, the tether loops can be cut and withdrawn from the system 10.

Yet another embodiment is depicted in FIGS. 8A-8C, showing alternative configurations of implant engaging elements. For example, the top view of FIG. 8A depicts pusher tube 40 with keyed projections 64B at the distal end that interlock within recesses 66 formed in a proximal hub or similar element of implant 5. When implant 5 is disposed within sheath 12, the inner diameter keeps projections 64B substantially aligned with the longitudinal axis of pusher tube 40, locking them into recesses 66 to prevent unrestrained distal motion of implant 5 during deployment. Once positioned at a desired location in the urethra 2, further relative distal displacement of implant 5 frees projections 64B from the constraint of sheath 12, allowing them to return to a preformed configuration that splay radially outward from the longitudinal axis of pusher tube 40 as shown in the side view of FIG. 8B, disengaging implant 5 from pusher rod 40. Alternatively, projections 64B may be controlled by any suitable mechanical linkage, such as by pivoting on hinges 68 when actuated by a puller wire extending through the lumen of pusher tube 40 as shown in the side view of FIG. 8C, with projections 64B deflecting either outward as depicted or inward. These designs allow implant 5 to be positioned at a desired radial orientation as the engagement between projections 64B and recesses 66 keep the components coupled, such that rotation of handle 16 can be translated to implant 5. As noted above, this can help position the arms of implant 5 so they do not align with the intra-lobular grooves of the prostate. Projections 64B can be formed from Nitinol, spring temper stainless steel, polymer, or other materials having resilience or can employ a mechanical linkage as noted. Further, the projections 64B could also be formed as part of implant 5 and configured to mate within recesses 66 of pusher tube 40. One or more keyed projections 64B may be made on the pusher tube 40 to lock with recesses 66 on the implant hub. Alternatively, the projections 64B may be made on the implant 5 to lock with recesses 66 on the pusher tube 40.

Figure 9A:
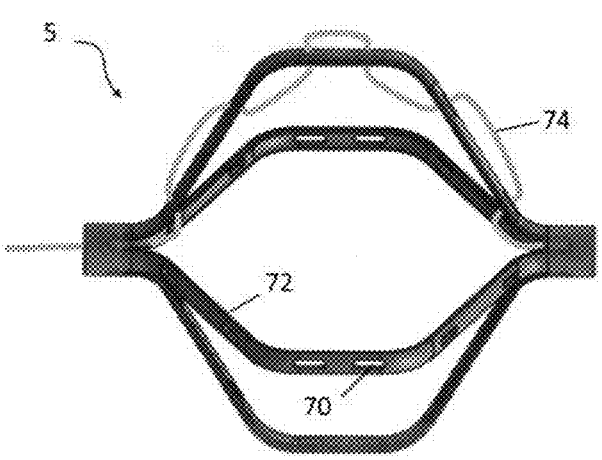
FIGS. 9A-C schematically depict implant engaging elements that constrain the implant according to various embodiments.
Figure 9B:
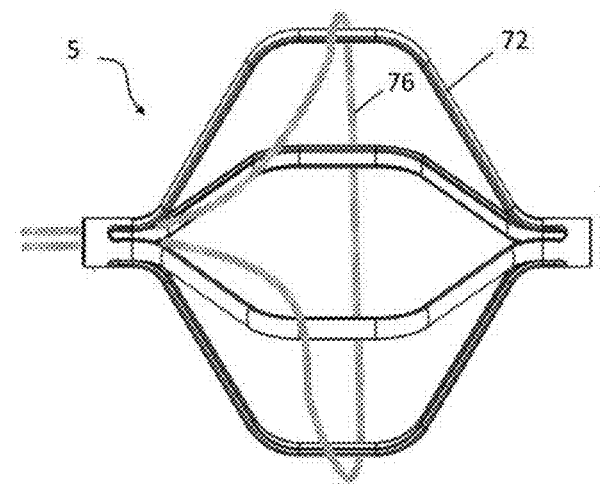
Figure 9C:
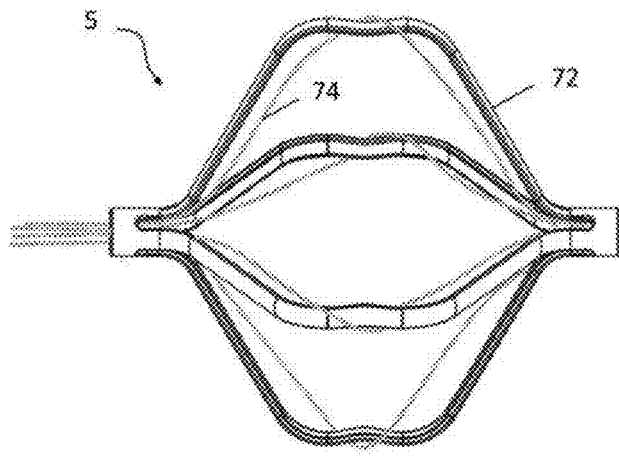

Additional features of this disclosure may be appreciated in reference to FIGS. 9A-C which show various exemplary implant 5 designs employing implant engaging elements 46 that are configured to help restrain implant 5 in a constrained configuration to facilitate deployment. In the embodiment of FIG. 9A, apertures 70 are created in low-strain, flat areas of the implant struts 72 or hubs so that the overall mechanical properties and integrity of the implant 5 are preserved. Preshaped wires 74 or threads are passed through apertures 70 in a route (for the sake of clarity, only one wire route is depicted) that will cause struts 72 to assume a constrained configuration by being substantially aligned with the longitudinal axis of implant 5 when tension is applied. Wires 74 may also assist controlled deployment and/or repositioning of implant 5 at the target site, as desired, by pulling the wires 74 and recollapsing a partially-deployed and wire-engaged implant 5 into delivery system 10. Once implant 5 is fully expanded or deployed at the target site, wire(s) 74 may be disengaged and the delivery system 10 may be removed. As desired, this wire 74 and slotted implant mechanism may also be used to constrain and deploy implant 5 without the need for a constraining sheath 12. It will be appreciated that any suitable variations on these designs may be employed with similar results. For example, FIG. 9B shows a lasso configuration in which loop 76 encircles struts 72 of implant 5. This design avoids the need to have apertures 70 in struts 72, but provides similar functionality in that tensions applied to loop 76 constrains implant 5 which can then be released to allow expansion once the desired position is achieved. Yet another example is depicted in FIG. 9C, which employs one wire 74 per strut 72. The middle sections of each strut 72 may have a concave configuration to help position wires 74. When tension is applied to wires 74 or loop 76, they compress implant struts 72 and constrain (or collapse) it into a low profile (small diameter) configuration. While the wires 74 or loop 76 are in tension, the implant 5 stays compressed. When under tension, each wire 74 or the loop 76 rests against the implant 5 surface with minimal gap. The wires or threads may be a single wire or a bundle as dictated by the particular configuration. They may be made from stainless steel, nitinol or other materials used to make wires and springs. They could also be made from strong, biocompatible polymeric materials, fabrics or threads used to make sutures or grafts.

Figure 10:
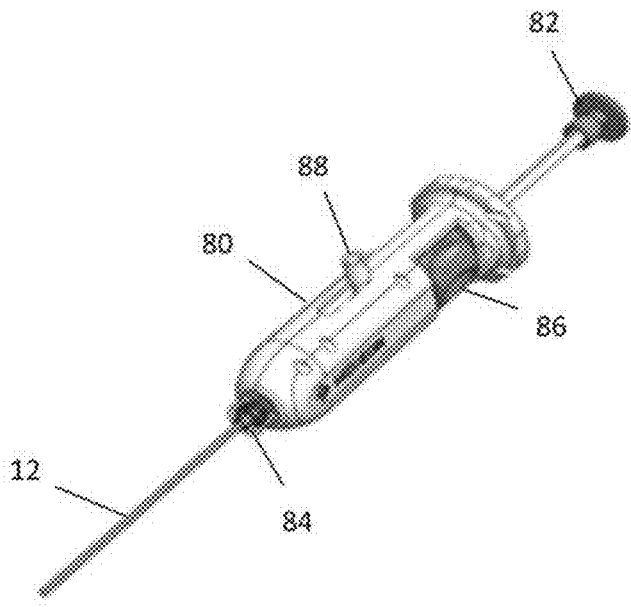
FIG. 10 schematically depicts a deployment device having a plunger actuator according to an embodiment.

In addition to the embodiments described above, it will be appreciated that various modifications to the devices and systems of this disclosure are within the scope of this disclosure. To help illustrate, FIG. 10 schematically illustrates an alternative handle having similar functionality with regard to deploying an implant 5 for treating or managing BPH. Notably, handle 80 is shown with plunger 82 for actuating pusher rod 40 as opposed to a slider. Implant 5, not shown here, is held in a constrained configuration within an elongated delivery sheath 12 in a manner consistent with the embodiments discussed above. Cystoscope locking luer 84 also functions similarly. Further, handle 80 has catheter advancement knob 86 that employs the techniques discussed above to adjust the position of the tip of the delivery sheath 12 and accurately position the device at the target site. Catheter position indicator 26 provides visual feedback of the length adjustment in conjunction with reference catheter position markers 28. Irrigation port 88 provides fluid communication for introducing saline for visualization during the procedure but in this embodiment is decoupled from pusher tube 40 movement. An implant engaging element 46 following the above teachings, along with the associated components, may be employed as desired.

Figure 11:
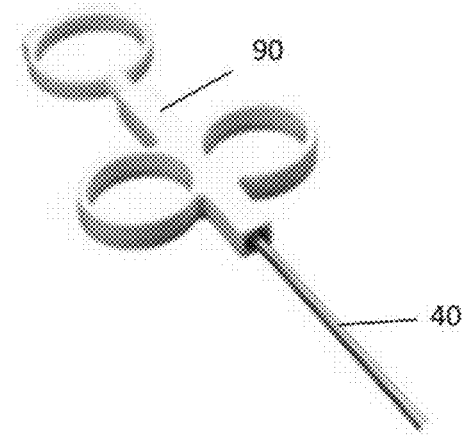
FIG. 11 schematically depicts a hand syringe deployment actuator according to an embodiment.

In yet another aspect, slider 32 of handle 16 or plunger 82 of handle 80 can be substituted with other suitable mechanisms for actuating distal movement of pusher tube 40 to deploy implant 5. For example, FIG. 11 schematically depicts hand syringe 90 to provide this functionality. In this embodiment, the implant 5 is similarly constrained inside a long flexible tube (a polymer sheath or a metallic coiled wire with a lumen). The inner lumen of the tube houses the implant 5 at the distal end of the tube in the constrained state. Pusher tube 40 engages the implant 5 and is coupled to the middle ring of syringe 90, so that when actuated, pushes and thereby deploys the implant 5 at the target site. In this embodiment, the delivery system does not incorporate an irrigation lumen or an implant engaging/disengaging element. A T-connector with two ports or a rotating hemostasis valve with two lumens may be connected to irrigation port of the working channel of the cystoscope. Irrigation is connected to one port of the T-connector or valve lumen. The second port and lumen with a seal and a sealing cap. The sealing cap is loosened, and the delivery system is introduced through the valve port. Once the delivery system is introduced, the valve is lightly tightened to prevent leaks during advancement of the delivery system. Once the delivery system is at the target site, the cap is fully tightened, and the implant 5 is deployed at the target site. After deployment, the valve is loosened, and the delivery system is retracted. Desirably, delivery systems employing syringe 90 adapt to different cystoscope lengths without the need for a long handle or need for an adjustment knob in the handle to adjust the catheter position during implant 5 deployment. It may be made with a longest length to fit all commercially available flexible cystoscopes. In this embodiment, irrigation is provided by fluid passage along through the working channel of the cystoscope along the outer surfaces of the delivery system. In other similar embodiments, features such as the implant engaging/disengaging element may be incorporated into the syringe as desired.

Treatment of LUTS associated with BPH requires accurate placement of an implant 5 of sufficient length in the prostatic urethra. Urethra length is often measured using abdominal or trans-rectal ultrasound from the bladder neck to the external sphincter. Accurate placement of the implant 5 requires knowledge of the prostatic urethra length from the bladder neck 6 to the verumontanum 7, which can only be measured by cystoscopy. There are few conventional measurement tools and devices to accurately measure the urethra length with or without the introduction of the measurement tool within the working channel of the flexible cystoscope. Accordingly, this disclosure also includes devices configured to accurately measure the prostatic urethra length between the bladder neck 6 and the verumontanum 7 using a cystoscope.

Figure 12:
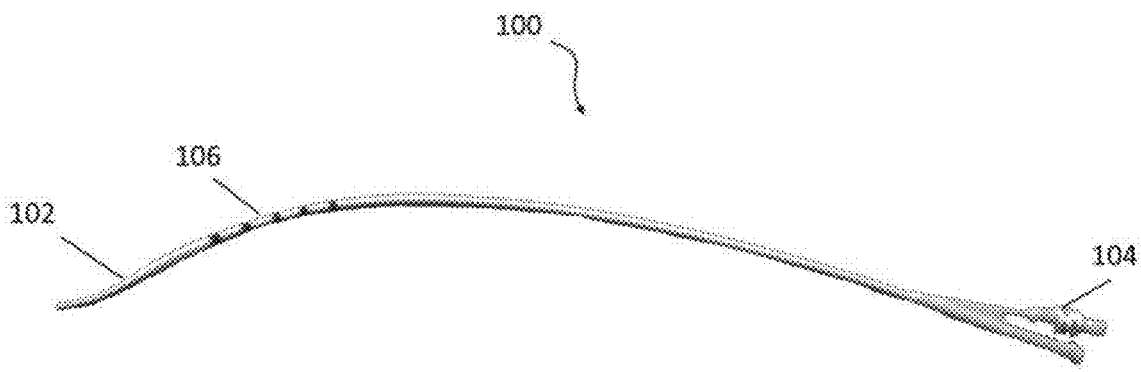
FIG. 12 schematically depicts a balloon catheter for determining appropriate implant length according to an embodiment.

As one illustration, FIG. 12 depicts a low-profile catheter 100, with a highly compliant balloon 102 on the distal end, that may be inserted through the working channel of the cystoscope or adjacent to the cystoscope. The balloon 102 on the distal end of the catheter 100 is inflated through side arm port 104 and light tension is applied to position it at the bladder neck 6 and the urethra 2 length from the bladder neck 6 to verumontanum 7 and the external sphincter are measured. Markers 106 aid in measuring urethra 2 length. Balloon 102 is deflated and catheter 100 is removed before the treatment procedure.

Figure 13:
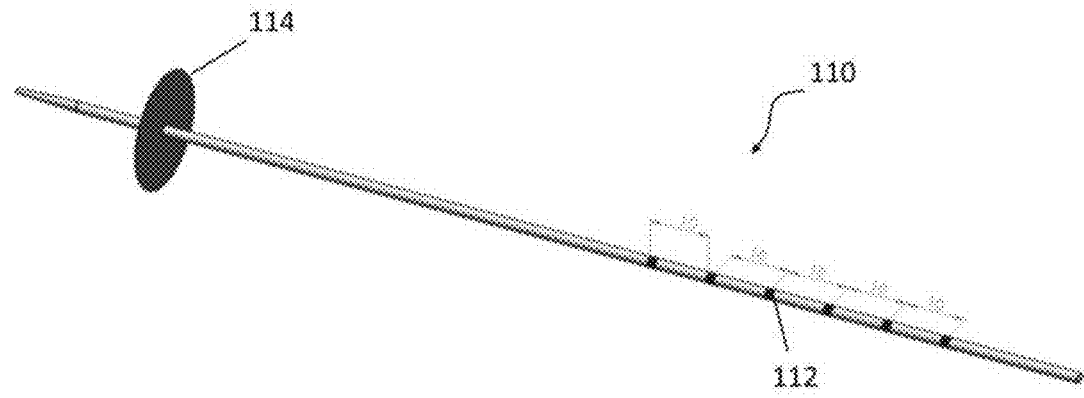
FIG. 13 schematically depicts a laser marker catheter for determining appropriate implant length according to an embodiment.

Yet another example is shown in FIG. 13, depicting laser marker catheter 110 that is also a low-profile (or diameter) hollow polymer tube that is compatible with the instrument channel of the cystoscope. It features graduation marks 112 and a radially projected laser light source 114 at the proximal end. Pre-determined length markers 112 on the distal body of catheter 110 are used to measure the prostatic urethra length. Catheter 110 is inserted through the instrument channel of the cystoscope and radial laser source 114 projects a laser mark within the urethra. Using this system, the user will hold the cystoscope steady at the pre-defined anatomical location, say at the verumontanum 7 for example, and continue to advance the laser marker catheter (24) forward, until the laser light projected by source 114 just disappears (out of cystoscope view), as catheter 110 approaches the bladder neck 6, and enters the urinary bladder 3. Counting the graduation marks 112 correspondingly determines the urethra 2 length. Catheter 110 may be inserted through the working channel of the cystoscope, or adjacent to the cystoscope. When the cystoscope and catheter 110 are introduced in tandem, they are both placed at the bladder neck 6, and the cystoscope is pulled back until the target site for deployment is within view. Again, counting the graduation marks 112 on the body of catheter 110 determines the urethra 2 length.

Accordingly, this disclosure encompasses devices, systems and methods of treatment for providing and deploying an implant to manage of urinary outflow obstruction symptoms and lower urinary tract symptoms associated with or caused by or secondary to benign prostatic hyperplasia. The implant is designed to satisfy several performance and operational criteria to overcome challenges in the treatment of BPH. The implant is adaptable for the range of potential prostate sizes, lengths and tissue morphologies that may be encountered in the adult male population. The implant is designed to resist migration due to urethra flow dynamics and movement once it is placed at the target site. The implant is also configured to permit placement and recovery using minimally invasive procedures using a flexible endoscope under local anesthesia (or topical anesthesia or no anesthesia). The implant is designed with minimal mass and surface area to prevent encrustation, while providing sufficient retraction force to push open the narrowing of the prostatic urethra. The implants are sized and shaped to be delivered and retrieved in a compressed configuration through traditional diagnostic imaging and delivery systems, such as traditional flexible cystoscopes used for urological procedures and that are used here to permit the delivery, visualization, deployment, and retrieval of the implant.

Methods for deployment and retrieval of the implant through a cystoscope under direct visualization, include retrieval and removal within one month to many years after implantation. The overall configuration of the device facilitates atraumatic removal through a catheter or a sheath into which the implant is contained by collapsing the implant to a reduced diameter and confining the implant at the distal end of a catheter, sheath, cystoscope or endoscope channel for atraumatic removal. The structural profile of the implant and delivery system design minimizes bleeding, swelling, spasm, or injury to the urethra during placement, while restoring urinary function, and eliminating the future risk of pain, sexual dysfunction, or urinary dysfunction. The design of the delivery system includes visible marking to allow the user to place the implant at a precise location relative to anatomical landmarks within the urethra. Such visible markings include marker bands, notches, color identification, graduated edges, diametrical changes on the delivery system. The design and placement of the device does not interfere with urinary function (prevents incontinence and facilitates urination upon activation of the external sphincter). The design and placement method also minimizes the potential for migration of the implant along the urethra and towards the bladder or towards the penis.

The implant exerts an expansion or tissue retraction force greater than 0.5N, or preferably greater than 2N, and most preferably between 5 and 30N along a substantial portion of the length of the implant, counteracting the compression forces directed radially and constricting the lumen along the urethra by the enlargements of prostatic tissue. Because the prostate has three lobes and is asymmetric, the implant preferably has 2 or 4 or more tissue-engaging regions such that the tissue contacting regions are not disposed within the three grooves formed by adjacent lateral and medial lobes of the prostate. If the design has 3 tissue engaging regions, the design is preferable asymmetric relative to the prostate physiology such that the implant is not disposed in the interlobular grooves. Instead, the tissue-engaging regions of the implant directly engage each of the three lobes of the prostate along the length for retracting the enlarged tissue to relieve and expand the fluid communication capacity or lumen of the urethra. Visual markings, such as marker bands, notches, coloration, etching, surface finish variations may be placed on the implant to facilitate visualization and accurate placement or deployment of the implant in the urethra.

The implant fits within a delivery system having an outer diameter (OD) less than 14 French and may have a diameter less than 6 French. The delivery system is able to advance with minimum resistance through the working instrument channel of the endoscope or cystoscope. In addition, the delivery system also incorporates sufficient free lumen to allow sufficient saline irrigation for sailing flow or fluid flow, typically with a minimum flow rate of 0.25 mL per second for direct visualization of the urethra during implant advancement and placement. The delivery system has a working port to connect to the irrigation source. In a preferred embodiment, the implant is confined in a collapsed configuration at the distal end of the delivery having a soft tip for atraumatic deployment of the implant. The delivery system is capable of being traversed by a guidewire having a soft tip at the most distal end and by a pusher rod or pusher tube ending just proximal of the implant.

In another embodiment, imaging elements are integrated into the delivery system. The imaging elements are compatible with existing video display systems made by Olympus, Stryker and Karl-Storz. The overall system profile is less than 26F (9 millimeters), or more preferably between 17-12F (6 millimeters) or smaller, to further minimize the pain during delivery and placement of the implant. Moreover, the integrated delivery system incorporating the implant and imaging elements may be a single-use or disposable medical device as compared to embodiments that are inserted through flexible and rigid cystoscopes that are resterilized and reusable.

The methods of the disclosure include methods of treatment of lower urinary tract symptoms associated with benign prostatic hyperplasia by implantation, and optionally subsequent retrieval, of the implant. The delivery systems are configured to maintain the implant in a compressed configuration at the distal end of an elongated sheath and deploy in an expanded configuration in the prostatic urethra.

Methods for implantation optionally include performing a diagnostic cystoscopy to determine the length of the prostatic urethra from the verumontanum to the bladder neck, such as with the devices disclosed above, followed by determining the diameter of the urethra and selection of an appropriately sized implant based, at least in part, on the diameter of the selected implant, which may be measured by the diameter of opposing tissue-engaging regions of the implant in the expanded configuration. Alternatively, diagnostic measurements of urethra length may also be obtained using abdominal ultrasound or trans-rectal ultrasound imaging methods. Measurement of urethra length from the bladder neck to the external sphincter may also be used to determine the appropriate implant size. In one deployment method, the clinician selects an implant having a pre-designated size that is maintained in a collapsed configuration at the distal end of the delivery system. The appropriately sized implant contained within the delivery system is introduced into the working channel of the cystoscope. The distal end of the delivery system is advanced, preferably under direct visualization, so that the distal end of the delivery system is proximal to the verumontanum for deployment. To improve implant deployment accuracy, the implant engaging elements noted above allow continued connection to the implant after expansion within the prostatic urethra allowing further adjustment.

Because the integrated device and delivery system are achieved with common surgical instruments, specifically with standard cystoscopes used with other urologic procedures, the implant can be placed and retrieved by an urologist without specialized equipment and under local anesthesia in an office environment and on an outpatient basis.

The methods of the disclosure include placement of the devices described herein within the urethra proximate to the prostate and below the bladder neck, including at specified distances between the bladder neck opening and external urinary sphincter. The methods include orienting the distal tip of a delivery system within the prostate and deploying the implant from a compressed to an expanded configuration. The methods also include orienting the device such that the contact regions of the implant engage a portion of the prostate away from the 3 apexes formed by the adjoining lobes of the prostate and to engage prostate tissue at a point spaced away from each apex.

Accordingly, the method can include visualization of the prostate lobes and respective apices during implantation and orientation of the implant using the delivery system to specifically engage portions of prostate tissue by the device to place the implant into the desired configuration with precise placement and orientation of the implant relative to all of the physiological structures along the length of the urethra within the transition (or T)-zone of the prostate and preferably distal to the bladder neck without obstructing the verumontanum. The method also includes the deployment of a plurality of implants selected and sized for the physiological condition of a particular BPH patient, including, the selective deployment of dissimilar embodiments of the implant as described herein and in the accompanying Figures.

The present application describes delivery systems to deliver an implant to the target location (the prostatic urethra), accurately deploy and place the implant, and retract the delivery system. Accordingly, the delivery systems may have several characteristics, including:

Able to hold the hold the mechanical implant in a constrained (compressed to a low-profile, or small diameter) configuration that is less than <14 F, ideally <6 F.

Atraumatic to the urethra and other anatomical structures during advancement, deployment and retraction.

Cause minimal pain or bleeding during use.

Sufficient length to reach the target site.

Compatible for use with existing or commercially-available or standard flexible cystoscope lengths (40-60 cm).

Sufficient flexibility to navigate the tortuosity of the urethra from the penis to the urinary bladder Do not impede the scope ability to visualize the anatomical features and landmarks (external sphincter, verumontanum, bladder neck and urinary bladder) during advancement and deployment.

Flexibility that allows articulation at the cystoscope tip.

Provide saline irrigation flow for imaging.

Incorporation with light-source and image-capture elements.

Accurate positioning the implant at the target location (such as within +/−5 mm from the target site; or within +/−2 mm).

Provide visual indicator to identify mechanical implant position.

Allow a single operator to complete the procedure (advance the delivery system to the prostatic urethra and implant the implant) without the assistance from a nurse or technician.

Implant deployment force that is clinically acceptable-not too high requiring high forces to deploy and not too low that may lead to premature deployment. Deployment force is to be less than <10 lbf, ideally <3 lbf.

Compatibility with standard video displays, such as VGA, smartphone or tablet.

Compatibility with workflow of urologists currently performing cystoscopies in the office.

Ability to secure/lock the implant in the constrained state and unlock before deployment.

Ability to adjust device working length to be compatible with various cystoscopes.

In some embodiments the actuation/articulating elements may be locked prior to disengaging the lock to deploy the implant.

In some embodiments the system further comprises an engaging/recapture element to reposition, orient and reorient the implant (relative to the anatomical landmarks) after deployment or implantation of the implant; and a disengaging mechanism to fully disconnect the implant from the delivery system.

It is also desirable to make the delivery system and the treatment steps as simple and easy as possible for the physician, thereby reducing the procedure time, complexity and the need for an assistant.

The exemplary embodiments disclosed above are merely intended to illustrate the various utilities of this disclosure. It is understood that numerous modifications, variations and combinations of functional elements and features of the present disclosure are possible in light of the above teachings and, therefore, within the scope of the appended claims, the present disclosure may be practiced otherwise than as particularly disclosed and the principles of this disclosure can be extended easily with appropriate modifications to other applications.

All patents and publications are herein incorporated for reference to the same extent as if each individual publication was specifically and individually indicated to be incorporated by reference. It should be understood that although the present disclosure has been specifically disclosed by preferred embodiments and optional features, modification and variation of the concepts herein disclosed may be resorted by those skilled in the art, and that such modifications and variations are considered to be within the scope of this disclosure.

What is claimed is:

1. A system for delivering and deploying an implant at a desired location in a lumen of a body, comprising:

an elongated sheath having an atraumatic tip at a distal end of the elongated sheath, the atraumatic tip having a lumen connecting an open proximal end and an open distal end, the elongated sheath being configured for introduction through a working channel of a cystoscope and having a lumen for maintaining the implant in a constrained configuration within the elongated sheath adjacent to the atraumatic tip;

a handle secured to a proximal end of the elongated sheath;

a pusher disposed within the elongated sheath and configured to push the implant out of the open distal end of the atraumatic tip at the desired location in the body lumen;

a deployment actuator associated with the handle and coupled to the pusher, wherein manipulation of the deployment actuator by a user results in relative motion between the pusher and the elongated sheath to cause the implant to be deployed from the open distal end of the atraumatic tip of the elongated sheath; and a rotation locking knob on the handle configured to selectively engage a luer connector hub of the cystoscope to prevent rotation of the delivery system relative to the cystoscope during deployment of the implant.

2. The system of claim 1, further comprising an advancement knob on the handle for adjusting a working length of the elongated sheath and implant deployment position.

3. The system of claim 1, wherein the deployment actuator is a slider coupled to a proximal end of the pusher.

4. The system of claim 1, wherein the manipulation of the deployment actuator retracts the elongated sheath to cause the implant to be deployed from the atraumatic tip of the elongated sheath.

5. The system of claim 1, wherein manipulation of the deployment actuator moves the pusher distally to cause the implant to be deployed from the atraumatic tip of the elongated sheath.

6. The system of claim 1, further comprising a fluid coupling associated with the handle in fluid communication within the elongated sheath configured to conduct irrigation fluid to the atraumatic tip.

7. The system of claim 6, wherein the fluid coupling is moveable with the deployment actuator.

8. The system of claim 1, further comprising an implant actuator associated with the handle connected to an implant engaging element and configured to selectively release or retract the implant during deployment.

9. The system of claim 7, further comprising an implant actuator connected to an implant engaging element and configured to selectively release the implant during deployment, wherein the implant engaging element is routed through the fluid coupling.

10. The system of claim 1, further comprising an implant engaging element configured to maintain control of the implant during deployment.

11. The system of claim 8, wherein the implant engaging element comprises a preformed shape disposed within the implant that is configured to retard distal movement of the implant when deployed.

12. The system of claim 8, wherein the implant engaging element comprises a releasable tether coupled to a proximal end of the implant.

13. The system of claim 8, wherein the implant engaging element comprises interlocking features at a distal end of the pusher and a proximal end of the implant.

14. The system of claim 8, wherein the implant engaging element comprises a wire routed through apertures formed in tissue-engaging portions of the implant that constrains the implant when tensioned.

15. The system of claim 8, wherein the implant engaging element comprises a wire routed around tissue-engaging portions of the implant that constrains the implant when tensioned.

16. A device for delivering and deploying an implant at a desired location in a lumen of a body, comprising:

an elongated sheath having an atraumatic tip at a distal end of the elongated sheath, the atraumatic tip having a lumen connecting an open proximal end and an open distal end, the elongated sheath being configured for introduction through a working channel of a cystoscope having a lumen for maintaining the implant in a constrained configuration within the elongated sheath adjacent to the atraumatic tip;

a handle secured to a proximal end of the elongated sheath;

a pusher coaxially disposed within the elongated sheath;

a deployment actuator associated with the handle and coupled to the pusher, wherein manipulation of the deployment actuator results in relative motion between the pusher and the elongated sheath to cause the implant maintained in the constrained configuration within the elongated sheath adjacent the atraumatic tip to be pushed out of the open distal end of the atraumatic tip of the elongated sheath at the desired location in the body lumen; and a rotation locking knob on the handle configured to selectively engage a luer connector hub of the cystoscope to prevent rotation of the delivery device relative to the cystoscope during deployment of the implant.

17. The device of claim 16, wherein manipulation of the deployment actuator moves the pusher distally to cause the implant to be deployed from the atraumatic tip of the elongated sheath.

18. The device of claim 16, further comprising an advancement knob on the handle for adjusting a working length of the elongated sheath and implant deployment location.

19. The device of claim 16, further comprising a fluid coupling associated with the handle in fluid communication with a lumen of the pusher configured to conduct irrigation fluid to the atraumatic tip.

20. The device of claim 19, wherein the fluid coupling is moveable with the deployment actuator.

21. The device of claim 16, wherein the elongated sheath is configured to fit within a working channel having a diameter not greater than 6 French.

22. The device of claim 16, wherein the handle further comprises a deployment lock that selectively restricts operation of the deployment actuator.

23. The device of claim 16, wherein the handle further comprises a connector coaxially disposed around the elongated sheath for engaging a lock of the working channel of the cystoscope.

24. A method for delivering and deploying an implant at a desired location in a lumen of body, comprising:

providing: i) an elongated sheath having an atraumatic distal tip at a distal end of the elongated sheath, the atraumatic tip having a lumen connecting an open proximal end and an open distal end, the elongated sheath being configured for introduction through a working channel of a cystoscope and having a lumen for maintaining the implant in a constrained configuration within the elongated sheath adjacent the atraumatic tip, ii) a handle secured to a proximal end of the elongated sheath, iii) a pusher disposed within the elongated sheath and configured to push the implant out of the open distal end of the atraumatic tip at the target site within the body lumen, iv) a deployment actuator associated with the handle and coupled to the pusher, wherein manipulation of the deployment actuator results in relative motion between the pusher and the elongated sheath to cause the implant to be deployed from the open distal end of the atraumatic tip of the elongated sheath, and v) a rotation locking knob on the handle configured to selectively engage a luer connector hub of the cystoscope to prevent rotation of the delivery system relative to the cystoscope during deployment of the implant;

introducing the elongated sheath through the working channel of the cystoscope;

positioning the distal tip at target site within the body lumen; and manipulating the deployment actuator to result in relative motion between the pusher and the elongated sheath to cause the implant to be pushed out of the open distal end of the atraumatic tip of the elongated sheath.

25. The method of claim 24, further comprising adjusting a working length of the elongated sheath before deployment of the implant.

26. The method of claim 24, further comprising manipulating an implant actuator to maintain control of the implant during deployment.

27. The method of claim 24, further comprising manipulating an implant actuator to release the implant after being driven distally out the elongated sheath.

28. The method of claim 24, further comprising determining an implant length by employing a balloon catheter or a laser marker catheter.

\* \* \* \* \*